United States Patent [19]

Shimada et al.

[11] Patent Number: 5,104,783

[45] Date of Patent: Apr. 14, 1992

[54] SILVER HALIDE COLOR PHOTOGRAPHIC MATERIAL

[75] Inventors: Yasuhiro Shimada; Seiji Ichijima, both of Kanagawa, Japan

[73] Assignee: Fuji Photo Film Co., Ltd., Kanagawa, Japan

[21] Appl. No.: 652,478

[22] Filed: Feb. 8, 1991

Related U.S. Application Data

[63] Continuation of Ser. No. 413,703, Sep. 28, 1989, abandoned.

[30] Foreign Application Priority Data

Oct. 4, 1988 [JP] Japan .................. 63-250332

[51] Int. Cl.$^5$ ................ G03C 1/08
[52] U.S. Cl. .................... 430/557; 430/556; 430/558; 430/543
[58] Field of Search ............ 430/558, 558 A, 557, 430/543, 556

[56] References Cited

U.S. PATENT DOCUMENTS 2,473,166  6/1949  Merckx .................. 430/558 X
4,239,894 12/1980  Seybold .................. 548/194
4,371,734  2/1983  Seybold .

FOREIGN PATENT DOCUMENTS 1252418 11/1971 United Kingdom .
2001094  1/1979 United Kingdom .
2105482  3/1983 United Kingdom .

Primary Examiner—Charles L. Bowers, Jr.
Assistant Examiner—Thomas R. Neville
Attorney, Agent, or Firm—Birch, Stewart, Kolasch & Birch

[57] ABSTRACT

The present invention relates to a silver halide color photographic material comprising a support having thereon at least one silver halide emulsion layer, wherein the silver halide color photograph material contains a coupler represented by the following general formula (I):

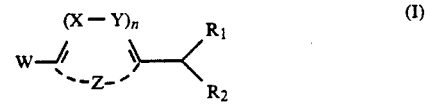

wherein X and Y each represents a nitrogen atom or a methine group; n represents 1 or 2, when n is 2, two X's and two Y's may be the same or different; Z represents a non-metallic atomic group necessary to form a heterocyclic ring or aromatic ring together with

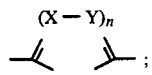

W represents a hydrogen atom or a group capable of being released upon a reaction with an oxidation product of a developing agent; and $R_1$ and $R_2$ each represents a substituent, and at least one of $R_1$ and $R_2$ represents an electron attractive sustituent.

The silver halide color photographic material containing the cyan dye forming coupler represented by the general formula (I) provides color images excellent in sharpness and preservability.

25 Claims, No Drawings

SILVER HALIDE COLOR PHOTOGRAPHIC MATERIAL

This application is a continuation of application Ser. No. 413,703, filed on Sep. 28, 1989, now abandoned.

FIELD OF THE INVENTION

The present invention relates to a silver halide color photographic material containing a novel cyan dye forming coupler.

BACKGROUND OF THE INVENTION

It is well known to employ so-called dye forming couplers (hereinafter simply referred to as couplers) which are capable of forming yellow, magenta or cyan dyes upon a coupling reaction with oxidation products of aromatic primary amine developing agents, in order to form color images in silver halide color photographic materials.

The principle of color photography using couplers and conventional examples of couplers are described, for example, in T. H. James, *The Theory of the Photographic Process*, Fourth Edition, Chapter 12, Macmillan Co. (1977) and *Research Disclosure*, No. 17643 (December, 1978).

As is apparently described in the above mentioned literature, phenols and naphthols have been hitherto employed as cyan couplers. However, since indoaniline dyes formed from these couplers have a small molecular absorption coefficient, large amount of couplers are requested in order to obtain sufficiently high image density. This is apparently disadvantageous, with respect to cost and also undesirable in view of the adverse influence on photographic performance More specifically, the incorporation of a large amount of couplers into an emulsion layer leads to an increase in the thickness of the emulsion layer, which causes an increase in the scattering of incident light at image exposure, resulting in degradation of sharpness.

For the purpose of solving this problem, specific types of couplers have been proposed as described in EP-A-249453. These couplers are certainly superior to conventional phenol or naphthol type couplers in view of a large molecular absorption coefficient. However, it has been found that fastness of color images obtained by these couplers is so poor that they cannot be employed in practice.

SUMMARY OF THE INVENTION

Therefore, an object of the present invention is to provide a silver halide color photographic material containing a novel cyan coupler.

Another object of the present invention is to provide a silver halide color photographic material which is advantageous in view of cost because a small amount of coupler can be employed by utilizing a cyan dye forming coupler having a large molecular absorption coefficient.

A further object of the present invention is to provide a silver halide color photographic material having a reduced thickness of the photographic layer which controls the scattering of incident light, resulting in improved sharpness by incorporating a cyan dye forming coupler having a large molecular absorption coefficient thereto.

A still further object of the present invention is to provide a silver halide color photographic material which provides cyan images excellent in fastness.

Other objects of the present invention will be apparent from the following detailed description and examples.

These objects of the present invention are accomplished by a silver halide color photographic material comprising a support having thereon at least one silver halide emulsion layer, wherein the silver halide color photographic material contains a coupler represented by the following general formula (I):

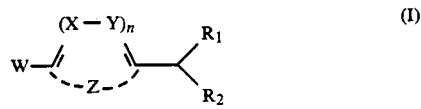

wherein X and Y each represents a nitrogen atom or a methine group; n represents 1 or 2; when n is 2, two X's and two Y's may be the same or different; Z represents a non-metallic atomic group necessary to form a heterocyclic ring or aromatic ring together with

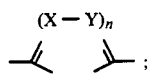

W represents a hydrogen atom or a group capable of being released upon a reaction with an oxidation product of a developing agent; and $R_1$ and $R_2$ each represents a substituent, and at least one of $R_1$ and $R_2$ represents an electron attractive substituent.

DETAILED DESCRIPTION OF THE INVENTION

The coupler represented by the general formula (I) preferably has a diffusion-resistant group. At least any one of $R_1$, $R_2$, X and Y preferably has an organic group having at least 10 carbon atoms.

The compound represented by the general formula (I) forms a dye represented by the general formula (D), described below upon a reaction with an oxidation product of an aromatic primary amine developing agent.

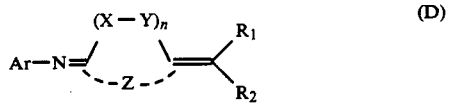

wherein Ar represents an aromatic group; and X, Y, Z, $R_1$, $R_2$ and n each has the same meaning as defined in the general formula (I).

Some of the dyes represented by the above described general formula (D) are disclosed in JP-B-62-60423 (the term "JP-B" as used herein means an "examined Japanese patent publication"). However, this patent publication discloses coloration of fiber using the above described dyes, and does not suggest the dye be used in color photographic light-sensitive materials. It is recognized first by the present inventors that the compound represented by the general formula (I) functions as a coupler and can be used in color photographic light-sensitive materials.

The dye formed from the coupler according to the present invention preferably has its maximum absorption wavelength in a range from 530 nm to 740 nm, particularly in a range from 600 nm to 700 nm.

The present invention includes the case wherein, in the compound represented by the general formula (I), $R_1$ and $R_2$, or $R_2$ and Z combine with each other at appropriate positions capable of being substituted to form a cyclic structure.

Now, the compound represented by the general formula (I) is explained in greater detail below.

In the general formula (I), X and Y each represents a nitrogen atom or a methine group which is represented by

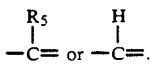

When X and Y each represents

$R_5$'s may be the same or different or they may combine with each other to form a ring. In the latter case, it is preferred to form a condensed ring, for example, a benzene condensed ring or a pyridine condensed ring.

In the above methine group, $R_5$ represents, for example, a halogen atom (for example, chlorine, or bromine), a straight chain, branched chain or cyclic, saturated or unsaturated, substituted or unsubstituted aliphatic group (for example, methyl, propyl, tert-butyl, trifluoromethyl, tridecyl, 3-(2,4-di-tert-amylphenoxy)propyl, 2-dodecyloxyethy, 3-phenoxypropyl, 2-hexylsulfonylethyl, cyclopentyl, benzyl, allyl, propargyl), a heterocyclic group (for example, 2-furyl, 2-thienyl, 2-pyrimidinyl, 2-benzothiazolyl), a cyano group, an alkoxy group (for example, methoxy, ethoxy, 2-methoxyethoxy, 2-dodecyloxyethoxy, 2-methanesulfonylethoxy), an aryloxy group (for example, phenoxy, 2-methylphenoxy, 4-tert-butylphenoxy), a heterocyclic oxy group (for example, 2-benzimidazolyloxy), an acyloxy group (for example, acetoxy, hexadecanoyloxy), a carbamoyloxy group (for example, N-ethylcarbamoyloxy), a silyloxy group (for example, trimethylsilyloxy), a sulfonyloxy group (for example, dodecylsulfonyloxy), an acylamino group (for example, acetamido, benzamido, tetradecanamido, α-(2,4-di-tert-amylphenoxy)butylamido, 2,4-di-tert-amylphenoxyacetamido, α-{4-(4-hydroxyphenylsulfonyl)phenoxy}decanamido, isopentadecanamido), an anilino group (for example, phenylamino, 2-chloroanilino, 2-chloro-5-tetradecanamidoanilino, 2-chloro-5-dodecyloxycarbonylanilino, N-acetylanilino, 2-chloro-5-{α-(2-tert-butyl-4-hydroxyphenoxy)dodecanamido}anilino), a ureido group (for example, phenylureido, methylureido, N,N-dibutylureido), an imido group (for example, N-succinimido, 3-benzylhydrazoinyl, 4-(2-ethylhexanoylamino)phthalimido), a sulfamylamino group (for example, N,N-dipropylsulfamoylamino, N-methyl-N-decylsulfamoylamino), an alkylthio group (for example, methylthio, octylthio, tetradecylthio, 2-phenoxyethylthio, 3-phenoxypropylthio, 3-(4-tert-butylphenoxy)propylthio), an arylthio group (for example, phenylthio, 2-butoxy-5-tert-octylphenylthio, 3-pentadecylphenylthio, 2-carboxyphenylthio, 4-tetradecanamidophenylthio), a heterocyclic thio group (for example, 2-benzothiazolylthio), an alkoxycarbonylamino group (for example, methoxycarbonylamino, tetradecyloxycarbonylamino), an aryloxycarbonylamino group (for example, phenoxycarbonylamino, 2,4-di-tert-butylphenoxycarbonylamino), a sulfonamido group (for example, methanesulfonamido, hexadecanesulfonamido, benzenesulfonamido, p-toluenesulfonamido, octadecanesulfonamido, 2-methoxy-5-tert-butylbenzenesulfonamido), a carbamoyl group (for example, N-ethylcarbamoyl, N,N-dibutylcarbamoyl, N-(2-dodecyloxyethyl)carbamoyl, N-methyl-N-dodecylcarbamoyl, N-{3-(2,4-di-tert-amylphenyoxy)propyl}carbamoyl), an acyl group (for example, acetyl, (2,4-di-tert-amylphenoxy)acetyl, benzoyl), a sulfamoyl group (for example, N-ethylsulfamoyl, N,N-dipropylsulfamoyl, N-(2-dodecyloxyethyl)sulfamoyl, N-ethyl-N-dodecylsulfamoyl, N,N-diethylsulfamoyl), a sulfonyl group (for example, methanesulfonyl, octanesulfonyl, benzenesulfonyl, toluenesulfonyl), a sulfinyl group (for example, octanesulfinyl, dodecylsulfinyl, phenylsulfinyl), an alkoxycarbonyl group (for example, methoxycarbonyl, butoxycarbonyl, dodecyloxycarbonyl, octadecyloxycarbonyl), an aryloxycarbonyl group (for example, phenoxycarbonyl, 3-petadecylphenoxycarbonyl), and an aromatic group having from 6 to 36 carbon atoms (for example, phenyl, naphthyl). When $R_5$ represents an aromatic group, it may have one or more substituents illustrated above.

In the general formula (I), Z represents an atom or an atomic group necessary to form a 5-membered ring or more, preferably a 5-membered to 8-membered ring, particularly preferably a 5-membered ring together with the carbon atoms connected thereto. A divalent group to form the ring includes a divalent amino group, an ether bond, a thioether bond, an alkylene group, an alkenylene group, an imino group, a sulfonyl group, a carbonyl group or a combination of two or more thereof. The divalent group may be substituted. A suitable substituent is selected from the substituents defined for $R_5$ described above. Z represents more preferably —O—, —S— or —X'=Y'— wherein X' and Y' each has the same meaning as defined for X and Y. Z represents particularly preferably —S—.

In the general formula (I), W represents a hydrogen atom or a group capable of being released when the coupler is reacted with an oxidation product of a developing agent (hereinafter simply referred to as a group capable of being released). When W represents a group capable of being released, the group capable of being released include a halogen atom, an aromatic azo group, a group wherein an aliphatic group, an aromatic group, a heterocyclic group, an aliphatic, aromatic or heterocyclic sulfonyl group or an aliphatic, aromatic or heterocyclic carbonyl group is connected to the coupling position through an oxygen, nitrogen, sulfur or carbon atom, or a heterocyclic group which connected to the coupling position through a nitrogen atom. The aliphatic group, aromatic group or heterocyclic group included in the group capable of being released may be substituted with one or more substituents selected from the substituents defined for $R_5$ described above. When two or more substituents are present, they may be the same or different. These substituents may be further substituted with one or more substituents selected from the substituents defined for $R_5$ described above.

The group capable of being released is a group capable of being released when the coupler is reacted with an oxidation product of a developing agent. Specific examples of the group capable of being released includes a halogen atom (for example, fluorine, chlorine, bromine), an alkoxy group (for example, ethoxy, dodecyloxy, methoxyethylcarbamoylmethoxy, carboxypropyloxy, methanesulfonylethoxy), an aryloxy group (for example, 4-chlorophenoxy, 4-methoxyphenoxy, 4-carboxyphenoxy), an acyloxy group (for example, acetoxy, tetradecanoyloxy, benzoyloxy), an aliphatic or aromatic sulfonyloxy group (for example, methanesulfonyloxy, toluenesulfonyloxy), an acylamino group (for example, dichloroacetylamino, heptafluorobutyrylamino), an aliphatic or aromatic sulonamido group (for example, methanesulfonamido, p-toluenesulfonamido), an alkoxycarbonyloxy group (for example, ethoxycarbonyloxy, benzyloxycarbonyloxy), an aryloxycarbonyloxy group (for example, phenoxycarbonyloxy), an aliphatic, aromatic or heterocyclic thio group (for example, ethylthio, 2-carboxyethylthio, phenylthio, tetrazolylthio), a carbamoylamino group (for example, N-methylcarbamoylamino, N-phenylcarbamoylamino), a 5-membered or 6-membered nitrogen-containing heterocyclic group (for example, imidazolyl, pyrazolyl, triazolyl, tetrazolyl, 1,2-dihydro-2-oxo-1-pyridyl), an imido group (for example, succinimido, hydantoinyl), and an aromatic azo group (for example, phenylazo). These groups may be substituted with one or more substituents selected from the substituents defined for $R_5$ described above. Further, another embodiment of the group capable of being released which is connected to the coupling position through a carbon atom is a bis type coupler obtained by condensation of two four-equivalent couplers with an aldehyde or ketone. The group capable of being released according to the present invention may contain a photographically useful group such as a development inhibiting group or a development accelerating group.

In the general formula (I), the electron attractive substituent represented by $R_1$ or $R_2$ is a substituent having the Hammett's substituent constant $\sigma_p$ of 0 or larger. Specific examples of the electron attractive group include a cyano group, a carbamoyl group (for example, N-phenylcarbamoyl, N-(2-chloro-5-tetradecyloxycarbonylphenyl)carbamoyl, N,N-diethylcarbamoyl, N-(2,4-dichlorophenyl)carbamoyl, N-(2-chloro-5-hexadecanesulfonamidophenyl)carbamoyl), an alkoxycarbonyl group (for example, ethoxycarbonyl, butoxycarbonyl, dodecyloxycarbonyl, 2-ethylhexyloxycarbonyl), an aryloxycarbonyl group (for example, phenoxycarbonyl, or 1-naphthyloxycarbonyl), an acyl group (for example, benzoyl, acetyl, 4-chlorobenzoyl, 2,4-dichlorobenzoyl), a sulfonyl group (for example, methanesulfonyl, dodecanesulfonyl, benzenesulfonyl, 2-butoxy-5-tert-octylphenylsulfonyl), a sulfamoyl group (for example, N-butylsulfamoyl, N-phenylsulfamoyl, N,N-diethylsulfamoyl), a nitro group, a fluorinated alkyl group (for example, trifluoromethyl, heptafluoropropyl), a sulfinyl group (for example, methanesulfinyl, benzenesulfinyl, naphthalenesulfinyl), and an aromatic group (for example, phenyl, 4-chlorophenyl, 4-acetamidophenyl).

The substituent represented by $R_1$ or $R_2$ includes an aliphatic group (for example, methyl, ethyl, octyl), an alkoxy group (for example, methoxy, ethoxy, dodecyloxy), or an amido group (for example, acetamido, pivalylamido, octaneamido).

$R_1$ or $R_2$ preferably represents a cyano group, a carbamoyl group, an alkoxycarbonyl group, an acyl group, a sulfonyl group or a sulfamoyl group. More preferably, at least one of $R_1$ and $R_2$ is an N-phenylcarbamoyl group. Particularly preferably, at least one of $R_1$ and $R_2$ is a group which is represented by

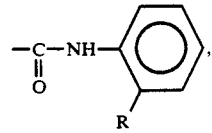

wherein R represents a group having a lone pair of electrons such as a halogen atom or a substituted or unsubstituted alkoxy group having from 1 to 18 carbon atoms, preferably R represents fluorine or chlorine.

n preferably represents 1.

Specific examples of the cyan couplers according to the present invention are set forth below, but the present invention should not be construed as being limited thereto.

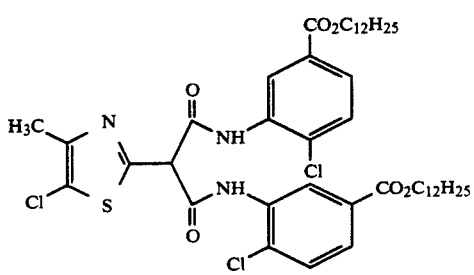

(1)

-continued
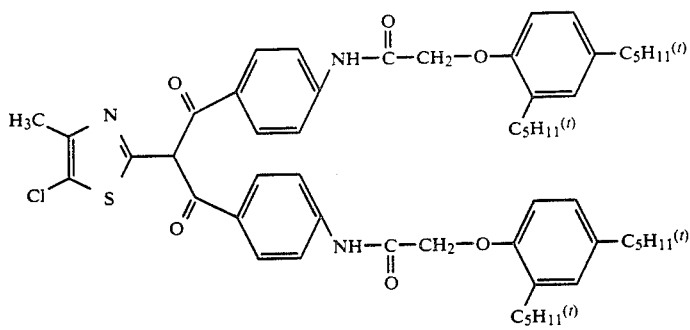
(2)
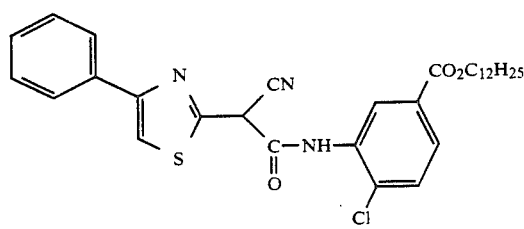
(3)
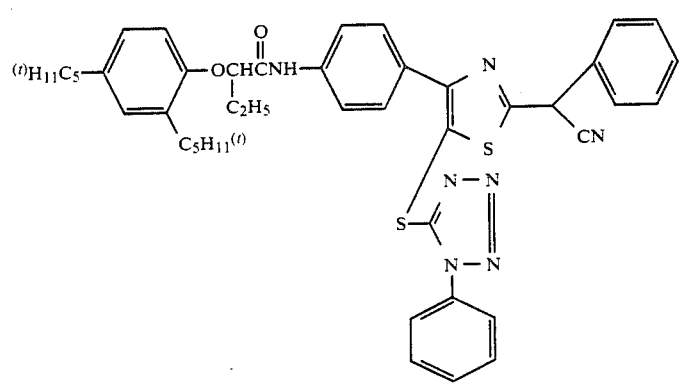
(4)
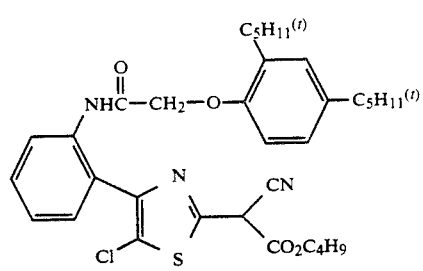
(5)
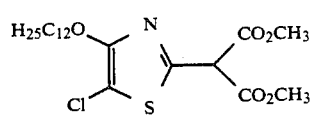
(6)
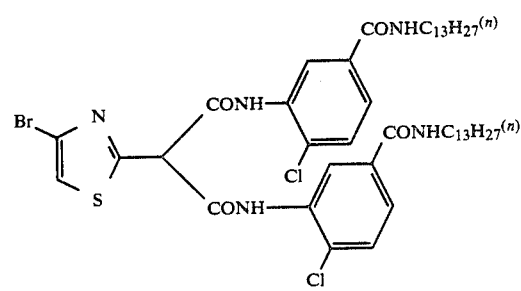
(7)

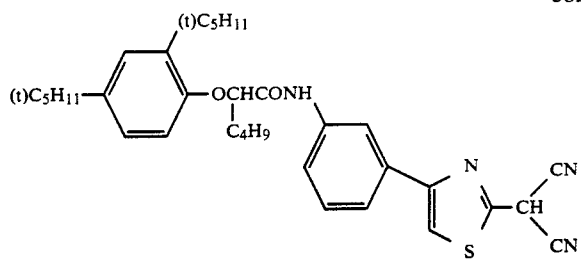
(8)
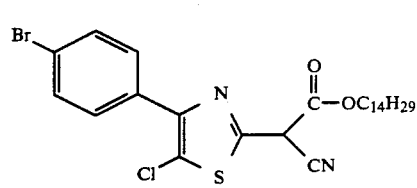
(9)
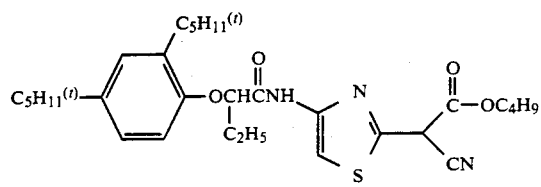
(10)
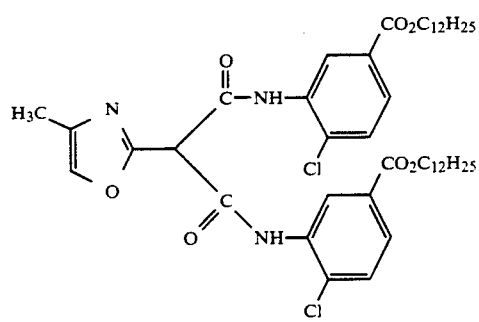
(11)
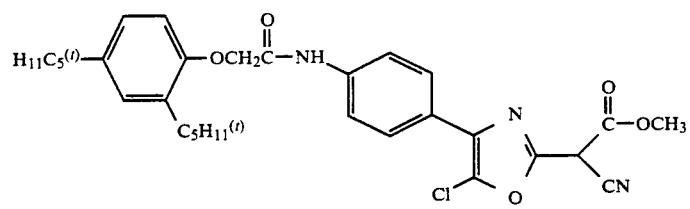
(12)
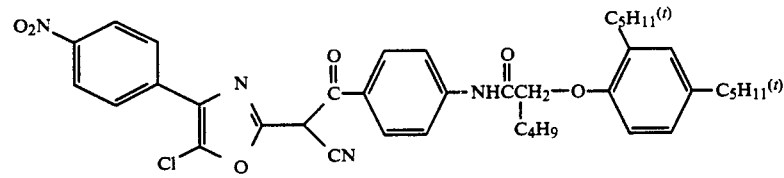
(13)
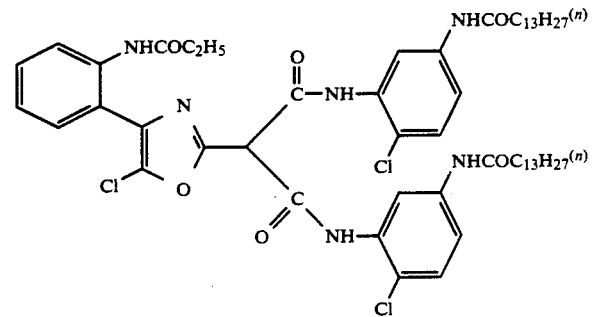
(14)

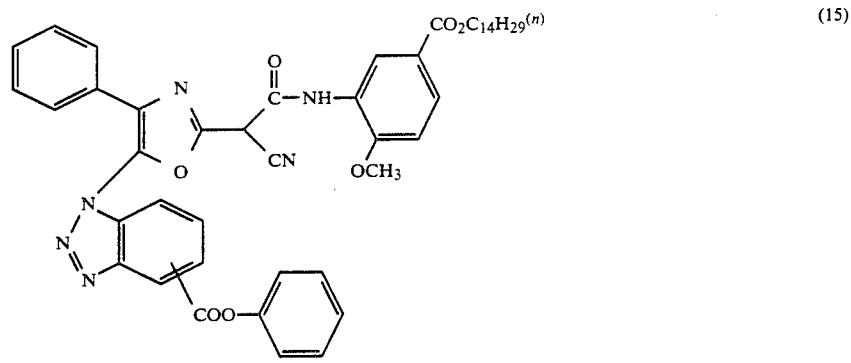
(15)
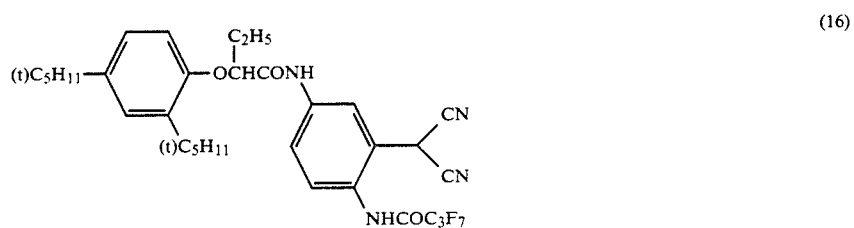
(16)
(17)
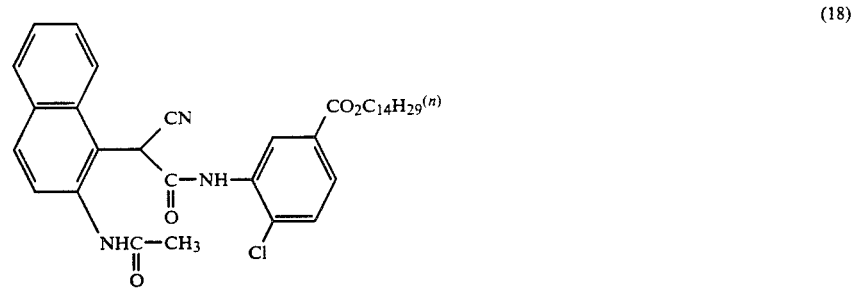
(18)
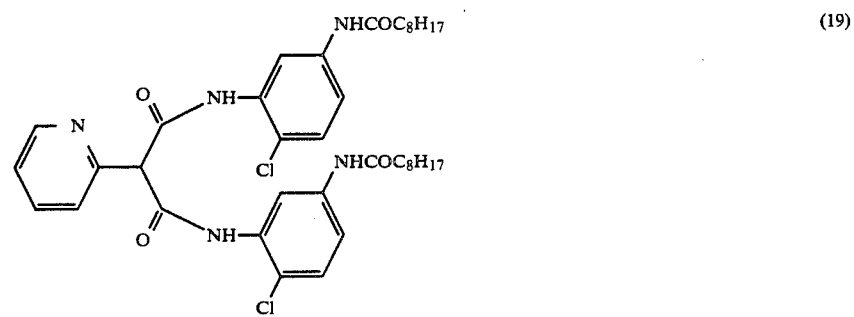
(19)

-continued
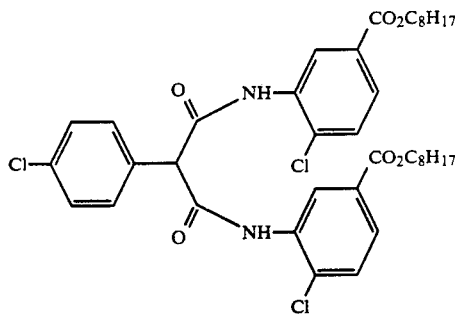 (20)
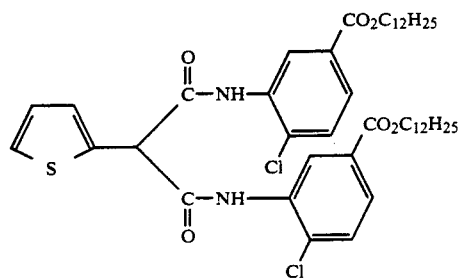 (21)
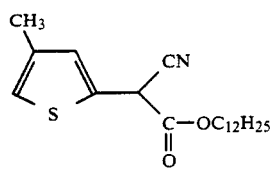 (22)
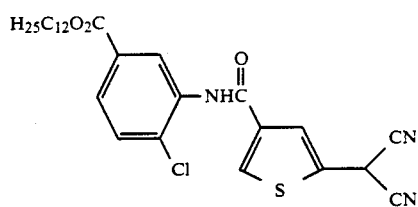 (23)
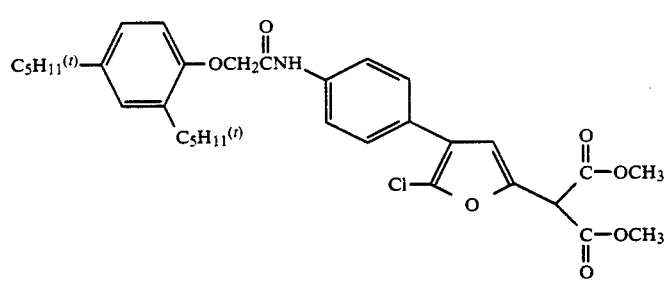 (24)
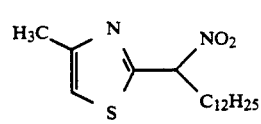 (25)
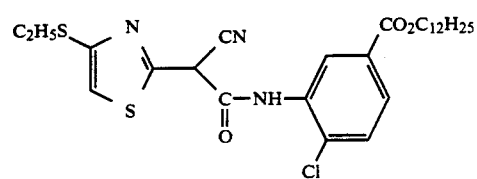 (26)

-continued
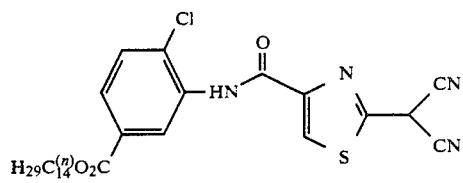
(27)
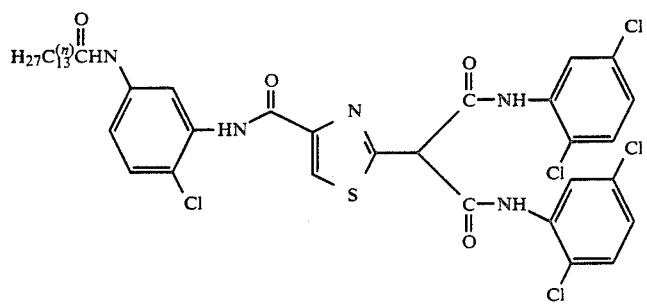
(28)
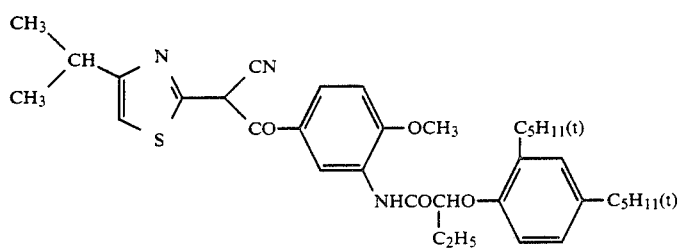
(29)
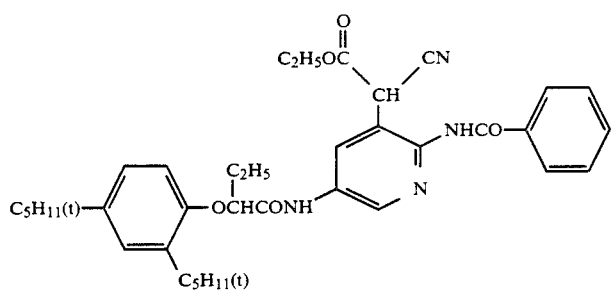
(30)
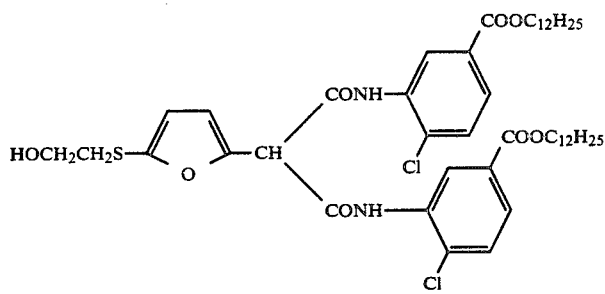
(31)
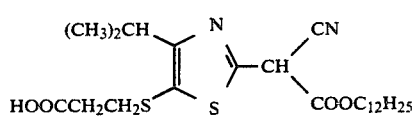
(32)

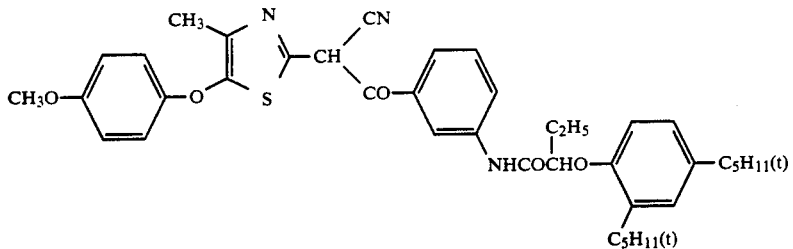
(33)
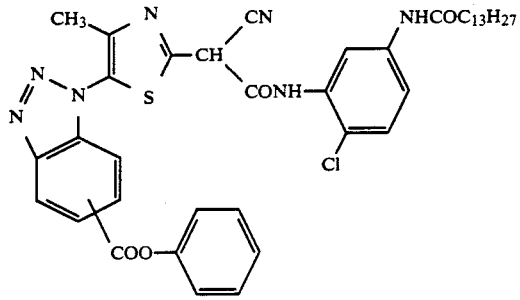
(34)
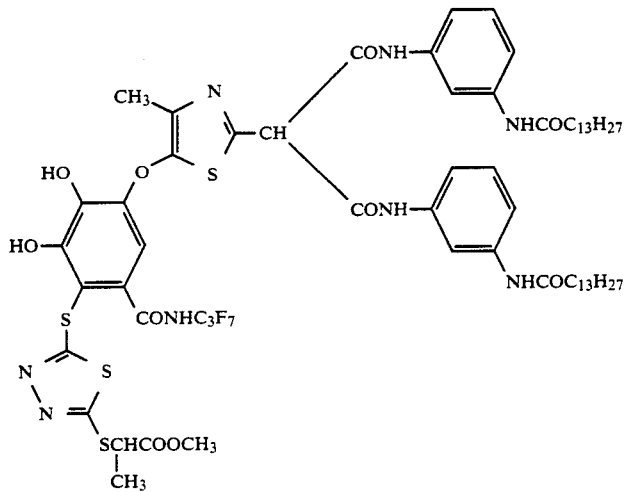
(35)
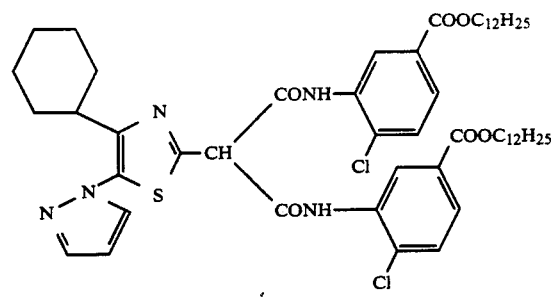
(36)
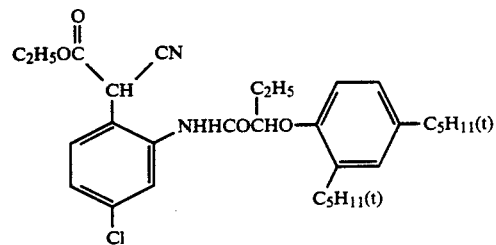
(37)

-continued
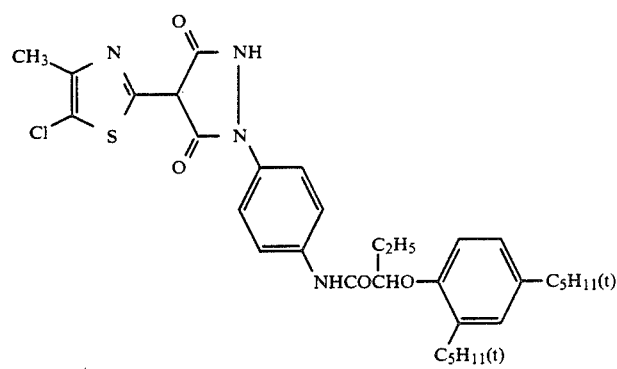 (38)
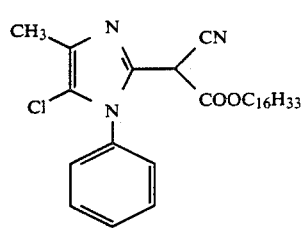 (39)
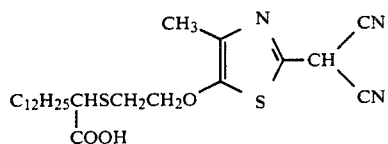 (40)
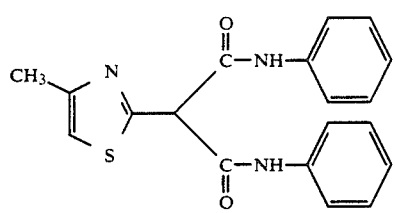 (41)
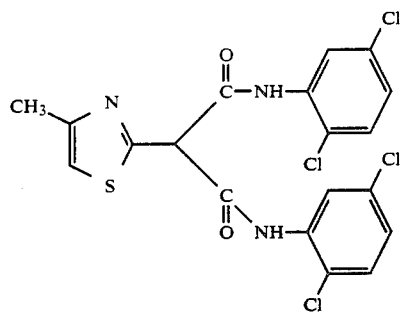 (42)
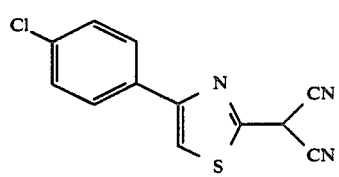 (43)
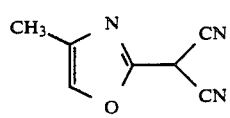 (44)

(45)

[Structure: phenyl-CONH-thiazole with CN and COCH₃ substituents]

(46)

[Structure: C₈H₁₇/C₆H₁₃-CHCH₂SO₂CH₂CH₂CONH-thiazole with CN and COCH₃]

(47)

[Structure: Cl-thiophene-CH(CN)(COOC₁₂H₂₅)]

The compounds according to the present invention can be synthesized by known methods. More specifically, they can be synthesized according to the methods as described, for example, in U.S. Pat. No. 4,371,734, *Chemistry Letters*, page 1761 (1987), *J. Prakt. Chemie*, No 317, page 771 (1975) and S. Gronowitz, *The Chemistry of Heterocyclic Compounds*, Vol. 44, Parts 1-3, John Wiley and Sons (1986), the methods as described in the literature cited therein or analogous methods thereto.

Now, synthesis examples of the compounds are specifically described below.

SYNTHESIS EXAMPLE 1

Synthesis of Compound (1)

Compound (1) was synthesized according to the following method.

[Structure (50): H₃C/Cl thiazole with CO₂C₂H₅ groups]

[Structure (51): H₂N-phenyl-CO₂C₁₂H₂₅ with Cl] → Compound (1)

10.0 g of Compound (50) was mixed with 27.8 g of Compound (51) and the mixture was stirred for 2 hours while maintaining the reaction temperature at 140° C. to 150° C. After the reaction, 300 ml of ethyl acetate was added to the reaction mixture while it was still hot and the mixture was stirred until the temperature fell to room temperature. The crystals deposited were collected by filtration to obtain 24.7 g (yield: 75.0%) of the desired Compound (1).

The structure of the compound was confirmed upon the observation of $(M+H)^+ = 808$ by a fast atom bombard ion mass spectrum (FAB-MS) positive detection method and elementary analysis.

|  | C (%) | H (%) | N (%) |
|---|---|---|---|
| Calculated | 66.91 | 7.74 | 5.21 |
| Found | 66.79 | 7.60 | 5.18 |

SYNTHESIS EXAMPLE 2

Synthesis of Compound (3)

Compound (3) was synthesized according to the following method.

[Structure (52): phenyl-thiazole with CN and CO₂C₂H₅] +

[Structure (51): H₂N-phenyl-CO₂C₁₂H₂₅ with Cl] → Compound (3)

15.0 of Compound (52) was mixed with 22.4 g of Compound (51) and the mixture was stirred for one hour while maintaining the reaction temperature at 140° C. to 150° C. Upon the same after-treatment as described in Synthesis Example 1, 25.6 g (yield: 82.0%) of the desired Compound (3).

The structure of the compound was confirmed upon the observation of $(M+H)^+ = 565$ by a fast atom bombard ion mass spectrum (FAB-MS) positive detection method and elementary analysis.

|  | C (%) | H (%) | N (%) |
|---|---|---|---|
| Calculated | 66.02 | 6.25 | 7.45 |

| | C (%) | H (%) | N (%) |
|---|---|---|---|
| Found | 64.91 | 6.02 | 7.40 |

SYNTHESIS EXAMPLE 3

Synthesis of Compound (7)

Compound (7) was synthesized according to the following method.

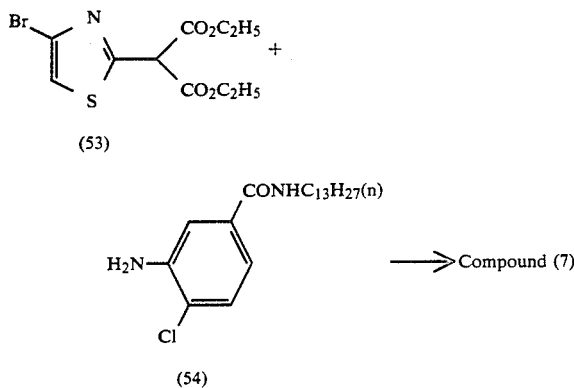

10.0 g of Compound (53) and 22.9 g of Compound (54) were dissolved in 100 ml of dimethylformamide and the solution was stirred for 2 hours while maintaining the reaction temperature at 120° C. to 130° C. After the reaction, 500 ml of ethyl acetate and 500 ml of water were added to the reaction mixture and the mixture was washed with water three times. The ethyl acetate layer was dried with magnesium sulfate, ethyl acetate was distilled off under a reduced pressure, and to the residue was added 100 ml of ethanol to recrystallize. The crystals deposited were collected by filtration to obtain 15.5 g (yield: 86.0%) of the desired Compound (7).

The structure of the compound was confirmed upon the observation of $(M+H)^+ = 935$ by a fast atom bombard ion mass spectrum (FAB-MS) positive detection method and elementary analysis.

| | C (%) | H (%) | N (%) |
|---|---|---|---|
| Calculated | 59.10 | 7.12 | 7.49 |
| Found | 58.85 | 6.82 | 7.62 |

SYNTHESIS EXAMPLE 4

Synthesis of Compound (11)

Compound (11) was synthesized according to the following method.

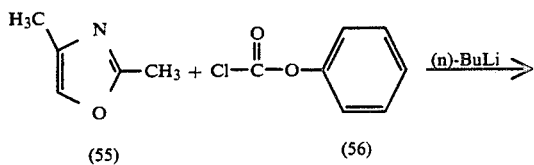

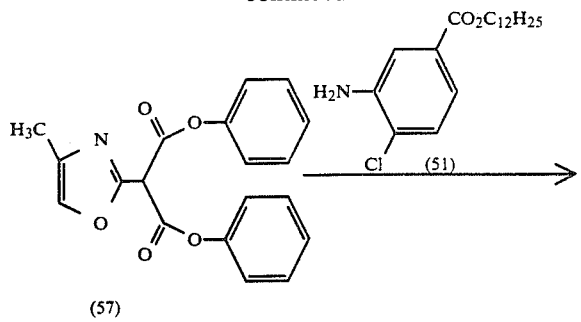

(57)

Compound (11)

Synthesis of Intermediate Compound (57)

1.0 g of Compound (55) was dissolved in 10 ml of anhydrous tetrahydrofuran and to the solution was added dropwise 6.8 ml of a 1.55 M hexane solution of (n)-butyl lithium over a period of 5 minutes under a nitrogen atmosphere while maintaining at −78° C. After the completion of addition, the mixture was stirred for 30 minutes while maintaining at −78° C., and then 5 ml of anhydrous tetrahydrofuran solution containing 1.6 g of Compound (56) dissolved therein was added thereto over a period of 10 minutes. After the reaction, 50 ml of ethyl acetate and 50 ml of water were added and the mixture was extracted three times. The ethyl acetate layer was dried with magnesium sulfate, ethyl acetate was distilled off under a reduced pressure, and to the residue was added 20 ml of ethanol to recrystallize. The crystals deposited were collected by filtration to obtain 2.2 g (yield: 65.0%) of Intermediate Compound (57).

Synthesis of Compound (11)

1.0 g of Compound (57) was mixed with 2.2 g of Compound (51), followed by the procedure described in Synthesis Example 1. The crystals deposited were collected by filtration to obtain 1.4 g (yield: 55%) of the desired Compound (11).

The structure of the compound was confirmed upon the observation of $(M+H)^+ = 828$ by a fast atom bombard ion mass spectrum (FAB-MS) positive detection method and elementary analysis.

| | C (%) | H (%) | N (%) |
|---|---|---|---|
| Calculated | 65.30 | 7.68 | 5.08 |
| Found | 65.53 | 7.74 | 5.28 |

Reference Experiment

In order to investigate the fundamental hue of the cyan dye formed from the coupler according to the present invention, Dyes (45), (46), (47) and (48) described below were synthesized using Compounds (41), (42), (43) and (44) respectively and the maximum absorption wavelength and molecular absorption coefficient thereof were measured.

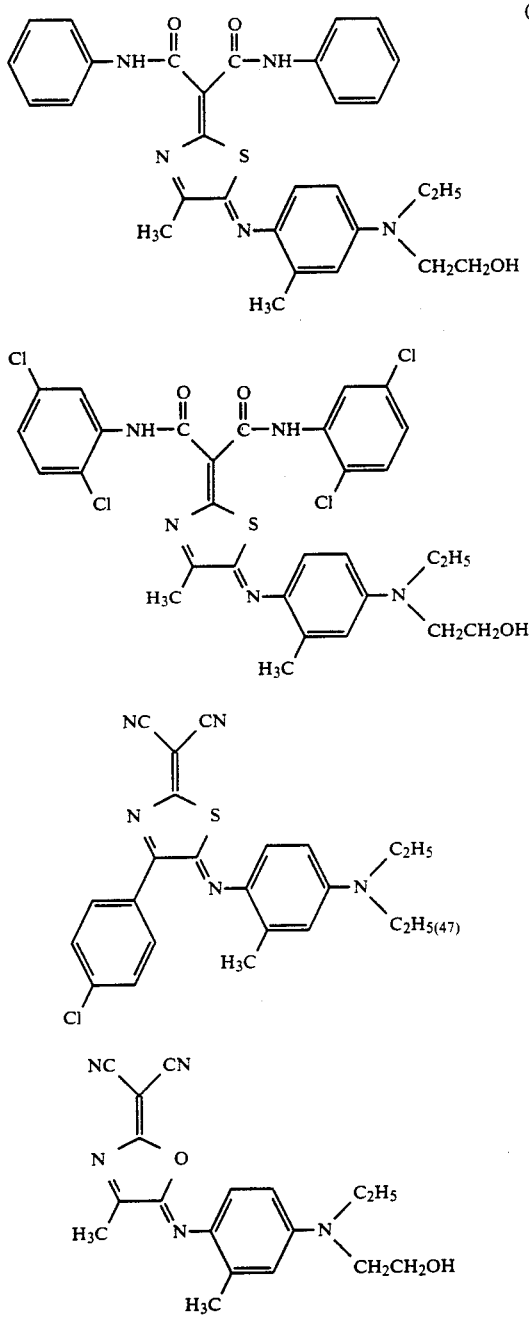

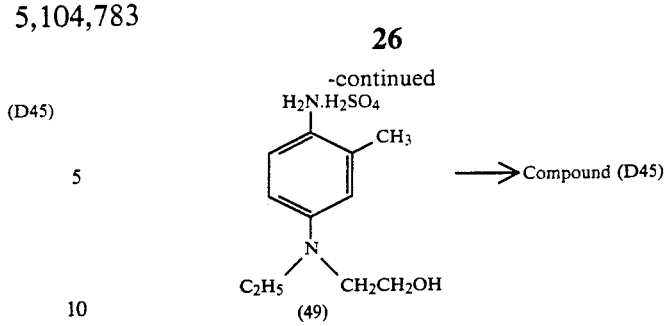

430 mg of Compound (41) was dissolved in 5 ml of ethanol and 3 ml of ethyl acetate, and to the resulting solution was added 5 ml of an aqueous solution containing 652 mg of sodium carbonate dissolved therein. Further, 644 mg of Compound (49) and 674 mg of ammonium persulfate were added thereto, and the mixture was stirred for 30 minutes. The crystals deposited were thoroughly washed with water and collected by filtration to obtain 250 mg of the desired Compound (45). The melting point of the compound was 195° C. to 196° C.

The structure of the compound was confirmed upon the observation of $(M+H)^+ = 542$ by a fast atom bombard ion mass spectrum (FAB-MS) positive detection method and elementary analysis.

|  | C (%) | H (%) | N (%) |
|---|---|---|---|
| Calculated | 66.54 | 5.78 | 12.95 |
| Found | 66.28 | 5.75 | 12.80 |

Compounds (46), (47) and (48) were synthesized in the same manner as described above. In Table 1 below, the maximum absorption wavelength and molecular absorption coefficient of the respective dye are described.

TABLE 1

| Dye | Maximum Absorption Wavelength (nm) | Molecular Absorption Coefficient[1] |
|---|---|---|
| (45) | 612.8 | $4.0 \times 10^4$ |
| (46) | 650.9 | $4.0 \times 10^4$ |
| (47) | 683.2 | $4.4 \times 10^4$ |
| (48) | 601.0 | $4.2 \times 10^4$ |
| Comparative Compound (1) | 644.3 | $2.7 \times 10^4$ |
| Comparative Compound (2) | 661.0 | $2.6 \times 10^4$ |

[1] $l \cdot mol^{-1} \cdot cm^{-1}$ unit

Compound (D45) was synthesized according to the method schematically shown below.

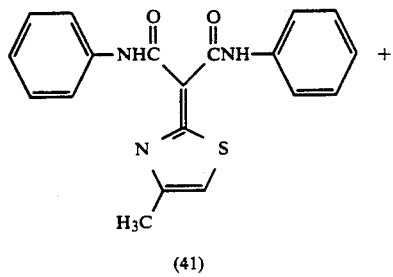

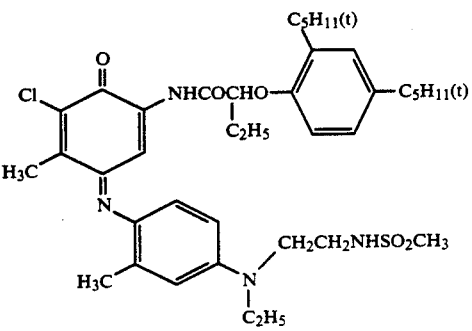

Comparative Compound (2)

-continued

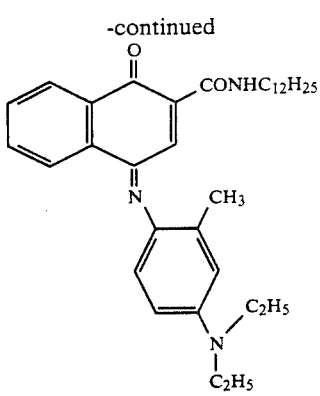

As is apparent from the results shown in Table 1 above, the couplers according to the present invention can provide dyes having a large molecular absorption coefficient in comparison with those formed from conventionally known phenol and naphthol type couplers.

The coupler according to the present invention is generally used in a range from 0.001 to 1 mol, preferably from 0.002 to 0.3 mol, per mol of light-sensitive silver halide. In case of color paper the coupler is generally employed in a range from $2 \times 10^{-4}$ to $9 \times 10^{-4}$ mol per m$^2$, and in case of color negative film the coupler is generally employed in a range from $0.5 \times 10^{-3}$ to $9 \times 10^{-3}$ mol per m$^2$.

In conventional color photography, the coupler according to the present invention is usually added to a red-sensitive emulsion layer or to a light-insensitive layer adjacent thereto.

The cyan coupler according to the present invention can be introduced into the photographic light-sensitive material by various known dispersing methods.

An oil droplet-in-water type dispersing method is most generally employed, and suitable examples of an organic solvent having a high boiling point which can be employed in the oil droplet-in-water type dispersing method are described, for example, in U.S. Pat. No. 2,322,027.

An organic solvent having a high boiling point but which has a boiling point not less than 175° C. at normal pressure is preferably employed in the oil droplet-in-water type dispersing method. Specific examples thereof include phthalic acid esters (for example, dibutyl phthalate, dicyclohexyl phthalate, di-2-ethylhexyl phthalate, decyl phthalate, bis(2,4-di-tert-amylphenyl) phthalate, bis(2,4-di-tert-amylphenyl) isophthalate, or bis(1,1-diethylpropyl) phthalate, phosphoric acid or phosphonic acid esters (for example, triphenyl phosphate, tricresyl phosphate, 2-ethylhexyl diphenyl phosphate, tricyclohexyl phosphate, tri-2-ethylhexyl phosphate, tridodecyl phosphate, tributoxyethyl phosphate, trichloropropyl phosphate, or di-2-ethylhexyl phenyl phosphonate), benzoic acid esters (for example, 2-ethylhexyl benzoate, dodecyl benzoate, or 2-ethylhexyl-p-hydroxybenzoate), amides (for example, N,N-diethyldodecanamide, N,N-diethyllaurylamide, or N-tetradecylpyrrolidone), alcohols or phenols (for example, isostearyl alcohol, or 2,4-di-tert-amylphenol), aliphatic carboxylic acid esters (for example, bis(2-ethylhexyl) sebacate, dioctyl azelate, gycerol tributyrate, isostearyl lactate, or trioctyl citrate), aniline derivatives (for example, N,N-dibutyl-2-butoxy-5-tert-octylaniline), and hydrocarbons (for example, paraffin, dodecylbenzene, or diisopropylnaphthalene).

Further, an organic solvent having a boiling point of at least about 30° C. and preferably having a boiling point above 50° C. but below about 160° C. can be used as an auxiliary solvent. Typical examples of auxiliary solvents include ethyl acetate, butyl acetate, ethyl propionate, methyl ethyl ketone, cyclohexanone, 2-ethoxyethyl acetate, or dimethylformamide.

The processes and effects of latex dispersing methods and specific examples of latexes for loading are described, for example, in U.S. Pat. No. 4,199,363, West German Patent Application (OLS) Nos. 2,541,274 and 2,541,230.

The color photographic light-sensitive material of the present invention may have at least one blue-sensitive silver halide emulsion layer, at least one green-sensitive silver halide emulsion layer and at least one red-sensitive silver halide emulsion layer on a support. The number of silver halide emulsion layers and light-insensitive layers and the order of arrangement thereof are not particularly restricted. One typical example is a silver halide photographic material comprising a support having thereon at least one light-sensitive layer group composed of a plurality of silver halide emulsion layers which have substantially the same spectral sensitivity but different speeds. The light-sensitive layer group is a unit light-sensitive layer having a spectral sensitivity to any of blue light, green light and red light. In a multilayer silver halide color photographic material, unit light-sensitive layers are generally arranged in the order of a red-sensitive layer, a green-sensitive layer and a blue-sensitive layer outwardly from the support. The order of arrangement of these layers can be modified depending on the purpose. Further, an arrangement wherein between two layers having the same spectral sensitivity, a light-sensitive layer having a different spectral sensitivity is sandwiched may be employed.

Between the above described silver halide light-sensitive layers or as the uppermost layer or the undermost layer, various light-insensitive layers such as an intermediate layer can be provided.

Into such a intermediate layer, couplers and DIR compounds as described, for example, in JP-A-61-43748, JP-A-59-113438, JP-A-59-113440, JP-A-61-20037 and JP-A-61-20038 may be incorporated (the term "JP-A" as used herein means an "unexamined published Japanese patent application"). Further, the intermediate layer may contain color stain preventing agents conventionally employed.

The plurality of silver halide emulsion layers which constitute the unit light-sensitive layer, preferably have a two layer construction comprises a high speed emulsion layer and a low speed emulsion layer as described, for example, in West German Patent 1,121,470 and British Patent 923,045. It is preferred that an arrangement is employed in which the lower speed layer is nearer the support. Further, a light-insensitive layer may be provided between silver halide emulsion layers. Moreover, a low speed emulsion layer may be provided further from the support while a high speed emulsion layer may be provided closer to the support as described, for example, in JP-A-57-112751, JP-A-62-200350, JP-A-62-206541 and JP-A-62-206543.

Specific examples of the layer arrangements include an arrangement in which a low speed blue-sensitive layer (BL), a high speed blue-sensitive layer (BH), a high speed green-sensitive layer (GH), a low speed green-sensitive layer (GL), a high speed red-sensitive layer (RH) and a low speed red-sensitive layer (RL) are arranged in this order from the outer layer to the support, an arrangement that BH, BL, GL, GH, RH and RL are arranged in this order from the outer layer to the support, or an arrangement that BH, BL, GH, GL, RL and RH are arranged in this order from the outer layer to the support.

Further, an arrangement may be employed in which a blue-sensitive layer, GH, RH, GL and RL are arranged in this order from the outer layer to the support as described in JP-B-55-34932. Moreover, an arrangement may be employed in which a blue-sensitive layer, GL, RL, GH and RH are arranged in this order from the outer layer to the support as described in JP-A-56-25738 and JP-A-62-63936.

Furthermore, an arrangement of three layers having different speeds comprising an upper silver halide emulsion layer having highest speed, an intermediate silver halide emulsion layer having lower speed than that of the upper layer, and an under silver halide emulsion layer having a lower speed than that of the intermediate layer as described in JP-B-49-15495 may also be employed. Thus, the speed decreases in sequence towards the support. Even if such an arrangement that three layers having different speeds are provided is employed, an intermediate speed emulsion layer, a high speed emulsion layer and a low speed emulsion layer may be arranged in this order from the outer layer to the support in the layers of the same spectral sensitivity as described in JP-A-59-202464.

As described above, various layer constructions and arrangements may be appropriately selected depending on the purpose of the photographic light-sensitive material.

In the photographic emulsion layers of the photographic light-sensitive material used in the present invention, a preferably employed silver halide is silver iodobromide, silver iodochloride or silver iodochlorobromide each containing about 30 mol % or less of silver iodide. Silver iodobromide or silver iodochlorobromide each containing from about 2 mol % to about 25 mol % of silver iodide is particularly preferred.

Silver halide grains in the silver halide emulsion may have a regular crystal structure, for example, a cubic, octahedral or tetradecahedral structure, an irregular crystal structure, for example, a spherical or tabular structure, a crystal defect, for example, a twin plane, or a composite structure thereof.

A particle size of silver halide may be varied and include from fine grains having about 0.2 micron or less to large size grains having about 10 microns of a diameter of projected area. Further, a polydisperse emulsion and a monodisperse emulsion may be used.

The silver halide photographic emulsion which can be used in the present invention can be prepared using known methods, for example, those as described in Research Disclosure, No. 17643 (December, 1978), pages 22 to 23, "I. Emulsion Preparation and Types" and ibid., No. 18716 (November, 1979), page 648, P. Glafkides, Chimie et Physique Photographique, Paul Montel (1967), G. F. Duffin, Photographic Emulsion Chemistry, The Focal Press (1966), and V. L. Zelikman et al., Making and Coating Photographic Emulsion, The Focal Press (1964).

Monodisperse emulsions as described, for example, in U.S. Pat. Nos. 3,574,628 and 3,655,394, and British Patent 1,413,748 are preferably used in the present invention.

Further, tabular silver halide grains having an aspect ratio of about 5 or more can be employed in the present invention. The tabular grains may be easily prepared by the method as described, for example, in Gutoff, Photographic Science and Engineering, Vol. 14, pages 248 to 257 (1970), U.S. Pat. Nos. 4,434,226, 4,414,310, 4,433,048 and 4,439,520, and British Patent 2,112,157.

Crystal structure of silver halide grains may be uniform, composed of different halide compositions between the inner portion and the outer portion, or may have a stratified structure.

Further, silver halide emulsions in which silver halide grains having different compositions are connected upon epitaxial junctions or silver halide emulsions in which silver halide grains are connected with compounds other than silver halide such as silver thiocyanate, or lead oxide may also be employed.

Moreover, a mixture of grains having a different crystal structure may be used.

The silver halide emulsions used in the present invention are usually conducted with physical ripening, chemical ripening and spectral sensitization. Various kinds of additives which can be employed in these steps are described in Research Disclosure, No. 17643, (December, 1978) and ibid., No. 18716 (November, 1979) and concerned items thereof are summarized in the table shown below.

Further, known photographic additives which can be used in the present invention are also described in the above mentioned literature and concerned items thereof are summarized in the table below.

| | Kind of Additives | RD 17643 | RD 18716 |
|---|---|---|---|
| 1. | Chemical Sensitizers | Page 23 | Page 648, right column |
| 2. | Sensitivity Increasing Agents | | Page 648, right column |
| 3. | Spectral Sensitizers and Supersensitizers | Pages 23 to 24 | Page 648, right column to page 649, right column |
| 4. | Whitening Agents | Page 24 | |
| 5. | Antifoggants and Stabilizers | Pages 24 to 25 | Page 649, right column |
| 6. | Light-Absorbers, Filter Dyes and Ultraviolet Ray Absorbers | Pages 25 to 26 | Page 649, right column to page 650, left column |
| 7. | Antistaining Agents | Page 25, right column | Page 650, left column to right column |
| 8. | Dye Image Stabilizers | Page 25 | |
| 9. | Hardeners | Page 26 | Page 651, left column |
| 10. | Binders | Page 26 | Page 651, left column |
| 11. | Plasticizers and Lubricants | Page 27 | Page 650, right column |
| 12. | Coating Aids and Surfactants | Pages 26 to 27 | Page 650, right column |
| 13. | Antistatic Agents | Page 27 | Page 650, right column |

Further, in order to prevent degradation of photographic property due to formaldehyde gas, it is preferred to add a compound capable of reacting with formaldehyde to fix it as described in U.S. Pat. Nos. 4,411,987 and 4,435,503 to the photographic light-sensitive material.

In the present invention, various color couplers can be employed and specific examples thereof are described in the patents cited in Research Disclosure, No. 17643, "VII-C" to "VII-G".

As yellow couplers used in the present invention, for example, those as described in U.S. Pat. Nos. 3,933,501, 4,022,620, 4,326,024, 4,401,752 and 4,248,961, JP-B-58-10739, British Patents 1,425,020 and 1,476,760, U.S. Pat. Nos. 3,973,968, 4,314,023 and 4,511,649, and European Patent 249,473A are preferred.

As magenta couplers used in the present invention, 5-pyrazolone type and pyrazoloazole type compounds are preferred. Magenta couplers as described, for example, in U.S. Pat. Nos. 4,310,619 and 4,351,897, European Patent 73,636, U.S. Pat. Nos. 3,061,432 and 3,725,064, *Research Disclosure*, No. 24220 (June, 1984), JP-A-60-33552, *Research Disclosure*, No. 24230 (June, 1984), JP-A-60-43659, JP-A-61-72238, JP-A-60-35730, JP-A-55-118034, JP-A-60-185951, U.S. pat. Nos. 4,500,630, 4,540,654 and 4,556,630, and WO (PCT) 88/04795 are particularly preferred.

In the present invention, known cyan couplers can be employed together with cyan coupler according to the present invention in the same or a different silver halide emulsion layer.

As cyan couplers used together in the present invention, phenol type couplers are exemplified. Cyan couplers as described, for example, in U.S. Pat. Nos. 4,052,212, 4,146,396, 4,228,233, 4,296,200, 2,369,929, 2,801,171, 2,772,162, 2,895,826, 3,772,002, 3,758,308, 4,334,011 and 4,327,173, West German Patent Application (OLS) No. 3,329,729, EP-A-121365, U.S. Pat. Nos. 3,446,622, 4,333,999, 4,451,559 and 4,427,767, and EP-A-161626 are preferred.

As colored couplers for correcting undesirable absorptions of dyes formed, those as described, for example, in *Research Disclosure*, No. 17643, "VII-G", U.S. Pat. No. 4,163,670, JP-B-57-39413, U.S. Pat. Nos. 4,004,929 and 4,138,258, and British Patent 1,146,368 are preferably employed.

As couplers capable of forming appropriately diffusible dyes, those as described, for example, in U.S. Pat. No. 4,366,237, British Patent 2,125,570, European Patent 96,570, and West German Patent Application (OLS) No. 3,234,533 are preferably employed.

Typical examples of polymerized dye forming couplers are described, for example, in U.S. Pat. Nos. 3,451,820, 4,080,211, 4,367,282, 4,409,320 and 4,576,910, and British Patent 2,102,173.

Couplers capable of releasing a photographically useful moiety during the course of coupling can be also employed preferably in the present invention. As DIR couplers capable of releasing a development inhibitor, those as described, for example, in the patents cited in *Research Disclosure*, No. 17643, "VII-F" described above, JP-A-57-151944, JP-A-57-154234, JP-A-60-184248, JP-A-63-37346, and U.S. Pat. No. 4,248,962 are preferred.

As couplers which release imagewise a nucleating agent or a development accelerator at the time of development, those as described, for example, in British Patents 2,097,140 and 2,131,188, JP-A-59-157638, and JP-A-59-170840 are preferred.

Furthermore, competing couplers such as those described, for example, in U.S. Pat. No. 4,130,427; polyequivalent couplers such as those described, for example, in U.S. Pat. Nos. 4,283,472, 4,338,393 and 4,310,618; DIR redox compound releasing couplers, DIR coupler releasing couplers, DIR coupler releasing redox compounds or DIR redox compound releasing redox compounds such as those described, for example, in JP-A-60-185950 and JP-A-62-24252; couplers capable of releasing a dye which turns to a colored form after being released such as those described, for example, in EP-A-173302; and bleach accelerating agent releasing couplers such as those described, for example, in *Research Disclosure*, No. 11449, ibid., No. 24241, and JP-A-61-201247 may be employed in the photographic light-sensitive material of the present invention.

Suitable supports which can be used in the present invention are described, for example, in *Research Disclosure*, No. 17643, page 28 and ibid., No. 18716, page 647, right column to page 648, left column, as mentioned above.

It is preferred that the total layer thickness of all hydrophilic colloid layer on the emulsion layer side of the photographic light-sensitive material according to the present invention is not more than 28 μm and a layer swelling rate of $T_{\frac{1}{2}}$ is not more than 30 seconds. The layer thickness means a thickness of layer measured after equilibration (2 days) at a temperature of 25° C. and relative humidity of 55%. The layer swelling rate of $T_{\frac{1}{2}}$ is determined according to known methods in the field of the art. For instance, a degree of swelling can be measured using a swellometer of the type described in A. Green, *Photogr. Sci. Eng.*, Vol. 19, No. 2, page 124 to 129, and $T_{\frac{1}{2}}$ is defined as a time necessary for reaching a half of a saturated layer thickness which is 90% of the maximum swelling layer thickness obtained when treated in a color developing solution at 30° C. for 3 minutes and 15 seconds.

The layer swelling rate of $T_{\frac{1}{2}}$ can be controlled by adding a hardening agent to a gelatin binder or changing the aging condition at coating.

The factor of swelling is preferably from 150% to 400%. The factor of swelling can be calculated by a formula of (maximum swelling layer thickness—layer thickness)/layer thickness wherein the maximum swelling layer thickness has the same meaning as defined above.

For the purpose of simplification and acceleration of processing, a color developing agent may be incorporated into the silver halide color photographic material according to the present invention. In order to incorporate the color developing agent, it is preferred to employ various precursors of color developing agents. Suitable examples of the precursors of developing agents include indoaniline type compounds as described in U.S. Pat. No. 3,342,597, Schiff's base type compounds as described in U.S. Pat. No. 3,342,599 and *Research Disclosure*, No. 14850 and ibid., No. 15159, aldol compounds as described in *Research Disclosure*, No. 13924, metal salt complexes as described in U.S. Pat. No. 3,719,492, and urethane type compounds as described in JP-A-53-135628.

Further, the silver halide color photographic material according to the present invention may contain, if desired, various 1-phenyl-3-pyrazolidones for the purpose of accelerating color development. Typical examples of the compounds include those as described, for example, in JP-A-56-64339, JP-A-57-144547, and JP-A-58-115438.

In the present invention, various kinds of processing solutions can be employed in a temperature range from 10° C. to 50° C. Although a standard temperature is from 33° C. to 38° C., it is possible to carry out the processing at higher temperatures in order to accelerate the processing whereby the processing time is shortened, or at lower temperatures in order to achieve improvement in image quality and to maintain stability of the processing solutions.

Further, for the purpose of saving an amount of silver employed in the color photographic light-sensitive material, the photographic processing may be conducted utilizing color intensification using cobalt or hydrogen peroxide as described in West German Patent 2,226,770 or U.S. Pat. No. 3,674,499.

Moreover, the silver halide color photographic material of the present invention can be applied to heat-developable light-sensitive materials as described, for example, in U.S. Pat. No. 4,500,626, JP-A-60-133449, JP-A-59-218443, JP-A-61-238056 and EP-A-210660.

The present invention can be applied to various color photographic light-sensitive materials, and typical examples thereof include color negative films for the general use or cinematography, color reversal films for slides or television, color papers, color positive films, and color reversal papers.

In accordance with the present invention, color images excellent in sharpness and in image preservability can be obtained. The compound represented by the general formula (I) for use in the present invention is excellent as a cyan coupler in that it has the coupling activity higher than that of the conventional phenolic or naphtholic cyan coupler and it forms a dye having no undesirable side-absorption in the blue region.

The present invention will be explained in greater detail with reference to the following examples, but the present invention should not be construed as being limited thereto.

EXAMPLE 1

On a paper support, both surfaces of which were laminated with polyethylene, were coated layers as shown below in order to prepare a multilayer color photographic light-sensitive material which was designated Light-Sensitive Material 1—1. The coating solutions were prepared in the following manner.

Preparation of Coating Solution for First Layer 19.1 g of Yellow coupler (ExY-1), 1.91 g of Polymer for dispersion (Cpd-1) and 0.46 g of Antifogging agent (Cpd-2) were dissolved in a mixture of 27.2 ml of ethyl acetate, 3.8 ml of Solvent (Solv-1) and 3.8 ml of Solvent (Solv-2), and the resulting solution was emulsified and dispersed in 185 ml of a 10% aqueous solution of gelatin containing 8 ml of a 10% aqueous solution of sodium dodecylbenzenesulfonate. Separately, to a silver chlorobromide emulsion (having a bromide content of 80.0 mol % and containing 70 g of silver per kg of the emulsion) was added $5.0 \times 10^{-4}$ mols of a blue-sensitive sensitizing dye shown below per mol of silver to prepare a blue-sensitive emulsion. The above described emulsified dispersion was mixed with the blue-sensitive silver chlorobromide emulsion, with the concentration of the resulting mixture being controlled, to form the composition shown below, i.e., the coating solution for the first layer.

Coating solutions for the second layer to the seventh layer were prepared in a similar manner as described for the coating solution for the first layer.

1-Oxy-3,5-dichloro-s-triazine sodium salt was used as a gelatin hardener in each layer.

The following spectral sensitizing dyes were employed in the emulsion layers, respectively.

Blue-Sensitive Emulsion Layer:

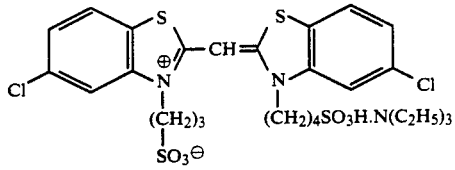

(Amount added: $5.0 \times 10^{-4}$ mol per mol of silver halide)

Green-Sensitive Emulsion Layer:

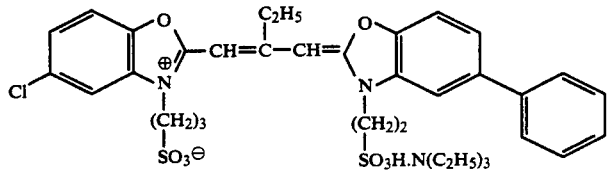

(Amount added: $4.0 \times 10^{-4}$ mol per mol of silver halide)

and

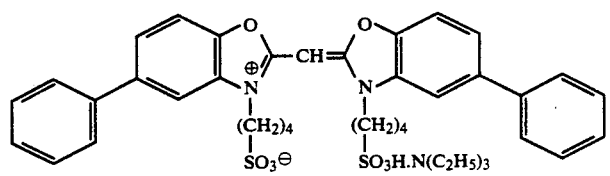

(Amount added: 7.0 × 10$^{-5}$ mol per mol of silver halide)

Red-Sensitive Emulsion Layer:

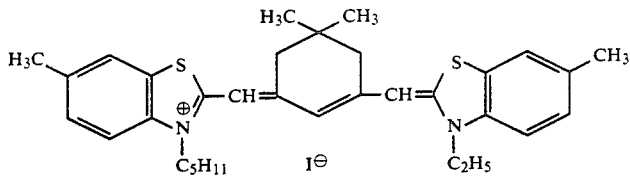

(Amount added: 0.9 × 10$^{-4}$ mol per mol of silver halide)

To the red-sensitive emulsion layer, was added the compound shown below in an amount of 2.6×10$^{-3}$ mol per mol of silver halide.

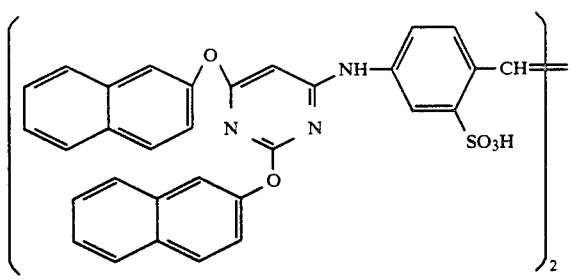

To the blue-sensitive emulsion layer and green-sensitive emulsion layer, was added 4-hydroxy-6-methyl-1,3,3a,7-tetraazaindene in amounts of 1.2×10$^{-2}$ mol and 1.1×10$^{-2}$ mol per mol of silver halide, respectively.

Further, to the green-sensitive emulsion layer, was added 1-(5-methylureidophenyl)-5-mercaptotetrazole in an amount of 1.0×10$^{-4}$ mol per mol of silver halide.

Moreover, to the red-sensitive emulsion layer, was added 2-amino-5-mercapto-1,3,4-thiadiazole in an amount of 3.0×10$^{-4}$ mol per mol of silver halide.

Furthermore, the following dyes were used as irradiation preventing dyes;

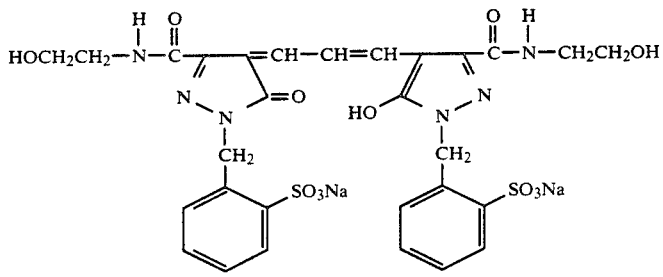

and

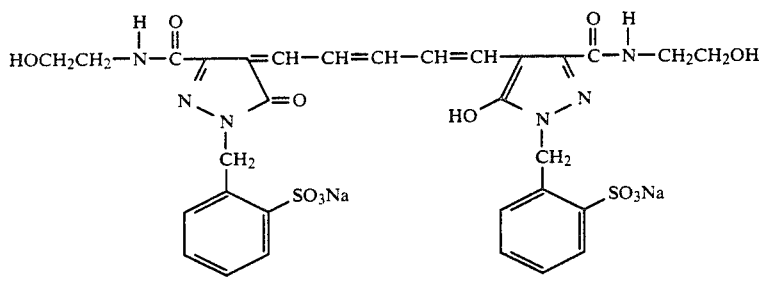

Layer Construction

The composition of each layer is shown below. The numerical values denote the coating amounts of components in g/m². The coating amount of silver halide emulsion is indicated in terms of silver coating amount.

| | | |
|---|---|---|
| Support | Paper support, both surfaces of which were laminated with polyethylene (the polyethylene coating containing a white pigment (TiO$_2$) and a bluish dye (ultramarine) on the first layer side) | |
| First Layer (Blue-sensitive layer) | Silver chlorobromide emulsion (Br: 80 mol %) | 0.26 |
| | Gelatin | 1.20 |
| | Yellow Coupler (ExY-1) | 0.66 |
| | Polymer for dispersion (Cpd-1) | 0.07 |
| | Antifogging agent (Cpd-2) | 0.02 |
| | Solvent (Solv-1) | 0.13 |
| | Solvent (Solv-2) | 0.13 |
| Second Layer (Color stain preventing layer) | Gelatin | 1.34 |
| | Color stain preventing agent (Cpd-3) | 0.04 |
| | Solvent (Solv-3) | 0.10 |
| | Solvent (Solv-4) | 0.10 |
| Third Layer (Green-sensitive layer) | Silver chlorobromide emulsion (Br: 80 mol %) | 0.14 |
| | Gelatin | 1.30 |
| | Magenta coupler (ExM-1) | 0.27 |

| | -continued | |
|---|---|---|
| | Color image stabilizer (Cpd-4) | 0.16 |
| | Color image stabilizer (Cpd-5) | 0.025 |
| | Color image stabilizer (Cpd-6) | 0.032 |
| | Solvent (Solv-3) | 0.21 |
| | Solvent (Solv-5) | 0.33 |
| Fourth Layer (Ultraviolet light absorbing layer) | Gelatin | 1.44 |
| | Ultraviolet light absorbing agent (UV-1) | 0.53 |
| | Color stain preventing agent (Cpd-3) | 0.05 |
| | Solvent (Solv-6) | 0.26 |
| Fifth Layer (Red-sensitive layer) | Silver chlorobromide emulsion (Br: 70 mol %) | 0.20 |
| | Gelatin | 0.89 |
| | Cyan coupler (ExC-1) | 0.30 |
| | Color image stabilizer (Cpd-5) | 0.004 |
| | Color image stabilizer (Cpd-6) | 0.007 |
| | Polymer for dispersion (Cpd-1) | 0.20 |
| | Color image stabilizer (Cpd-7) | 0.07 |
| | Antifogging agent (Cpd-2) | 0.01 |
| | Solvent (Solv-1) | 0.19 |
| Sixth Layer (Ultraviolet light absorbing layer) | Gelatin | 0.47 |
| | Ultraviolet light absorbing agent (UV-1) | 0.17 |
| | Solvent (Solv-2) | 0.08 |
| Seventh Layer (Protective layer) | Gelatin | 1.25 |
| | Acryl-modified polyvinyl alcohol copolymer (Degree of modification: 17%) | 0.05 |
| | Liquid paraffin | 0.02 |

The compounds used in the above-described layers have the structures shown below respectively.

Yellow coupler (ExY-1)

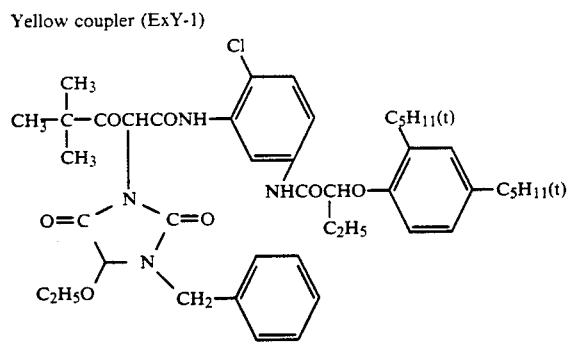

Magenta coupler (ExM-1)

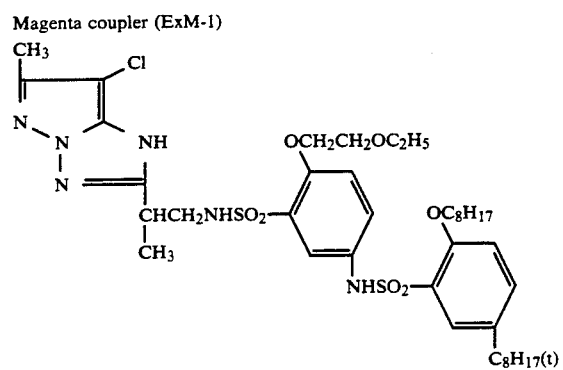

Cyan coupler (ExC-1) (corresponding to Compound (1))

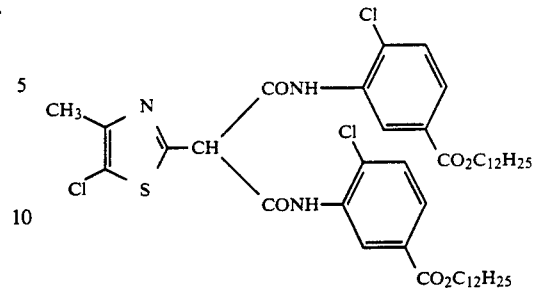

Polymer for dispersion (Cpd-1)

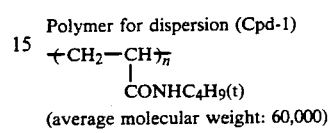

(average molecular weight: 60,000)

Antifogging agent (Cpd-2)

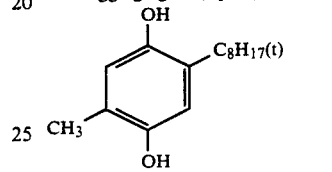

Color stain preventing agent (Cpd-3)

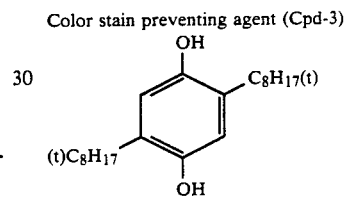

Color image stabilizer (Cpd-4)

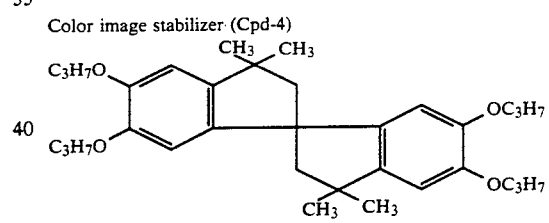

Color image stabilizer (Cpd-5)

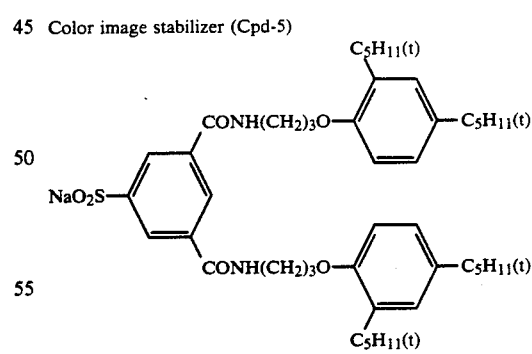

Color image stabilizer (Cpd-6)

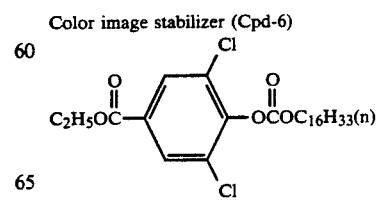

Color image stabilizer (Cpd-7)
A mixture of

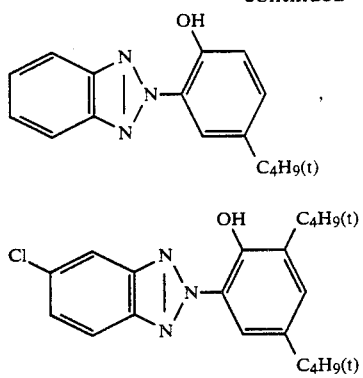

and

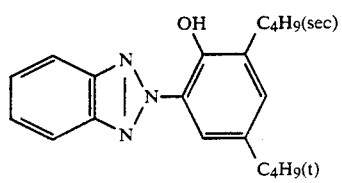

in a weight ratio of 4:2:5.

Ultraviolet light absorbing agent (UV-1)
A mixture of

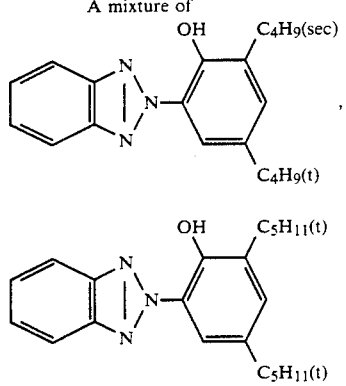

and

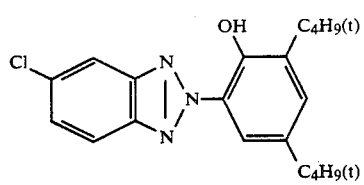

in a weight ratio of 12:10:3.

Solvent (Solv-1)

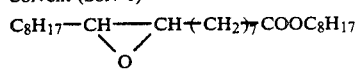

Solvent (Solv-2)
O=P⁅O—C₉H₁₉—iso)₃

Solvent (Solv-3)

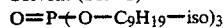

Solvent (Solv-4)

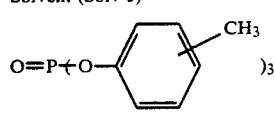

Solvent (Solv-5)

$O=P(OCH_2\overset{C_2H_5}{\underset{|}{CH}}C_4H_9)_3$

Solvent (Solv-6)

$$\begin{array}{c} COOCH_2\overset{C_2H_5}{\underset{|}{CH}}C_4H_9 \\ | \\ (CH_2)_8 \\ | \\ COOCH_2\overset{|}{\underset{C_2H_5}{CH}}C_4H_9 \end{array}$$

Light-Sensitive Materials 1-2 to 1-8 were prepared in the same manner as described for Light-Sensitive Material 1—1 except for using the equimolar amount of cyan couplers described in Table 2 below in the case of Light-Sensitive Materials 1-2 to 1-6 and 1-8, and 1.6 time molar amounts of cyan coupler described in Table 2 below in the case of Light-Sensitive Material 1-7, in place of the cyan coupler employed in Light-Sensitive Material 1—1, respectively.

TABLE 2

| Light-Sensitive Material | Cyan Coupler | Remark |
| --- | --- | --- |
| 1-1 | (1) | Present Invention |
| 1-2 | (2) | Present Invention |
| 1-3 | (5) | Present Invention |
| 1-4 | (9) | Present Invention |
| 1-5 | (14) | Present Invention |
| 1-6 | (33) | Present Invention |
| 1-7 | Comparative Compound A | Comparison |
| 1-8 | Comparative Compound B | " |

Comparative Compound A

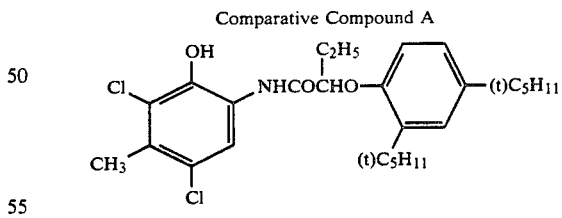

Compound B (described in EP 249,453)

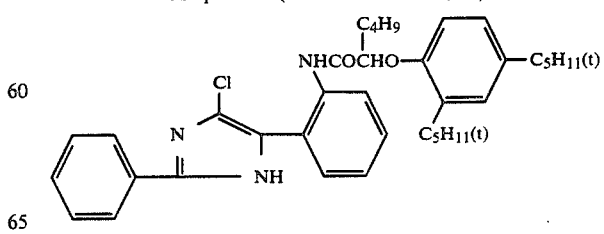

Light-Sensitive Materials 1—1 to 1-8 thus-prepared were exposed to light through an optical wedge and then subjected to development processing according to the following processing steps.

| Processing Step | Temperature (°C.) | Time |
|---|---|---|
| Color Development | 38 | 1 min. 40 sec. |
| Bleach-Fixing | 35 | 60 sec. |
| Rinse (1) | 33 to 35 | 20 sec. |
| Rinse (2) | 33 to 35 | 20 sec. |
| Rinse (3) | 33 to 35 | 20 sec. |
| Drying | 70 to 80 | 50 sec. |

The composition of each processing solution used was as follows:

| Color Developing Solution | |
|---|---|
| Water | 800 ml |
| Diethylenetriaminepentaacetic acid | 1.0 g |
| Nitrotriacetic acid | 2.0 g |
| 1-Hydroxyethylidene-1,1-diphosphonic acid | 2.0 g |
| Benzyl alcohol | 16 ml |
| Diethylene glycol | 10 ml |
| Sodium sulfite | 2.0 g |
| Potassium bromide | 0.5 g |
| Potassium carbonate | 30 g |
| N-Ethyl-N-(β-methanesulfonamidoethyl)-3-methyl-4-aminoaniline sulfate | 5.5 g |
| Hydroxylamine sulfate | 2.0 g |
| Brightening agent (WHITEX 4, manufactured by Sumitomo Chemical Co., Ltd.) | 1.5 g |
| Water to make | 1.000 ml |
| pH (at 25° C.) | 10.20 |
| Bleach-Fixing Solution | |
| Water | 400 ml |
| Ammonium thiosulfate (70% soln.) | 80 ml |
| Ammonium sulfite | 24 g |
| Ammonium ethylenediaminetetraacetato ferrate | 30 g |
| Disodium ethylenediaminetetraacetate | 5 g |
| Water to make | 1,000 ml |
| pH (at 25° C.) | 6.50 |

Rinse Solution

Ion exchanged water (contents of calcium and magnesium each being not more than 3 ppm).

Each sample thus-obtained was cut into two parts, one part was stored at 5° C. and the other part was preserved at 60° C. and 70% of relative humidity for 8 weeks in order to evaluate image fastness thereof.

Cyan density of the sample subjected to the fading test at the point corresponding to the point having 1.0 of cyan density in the sample stored at 5° C. was measured whereby a remaining rate of cyan color image was determined.

The results obtained are shown in Table 3 below.

TABLE 3

| Sample | Remaining rate of Cyan Color Image (%) |
|---|---|
| 1-1 (Present Invention) | 88 |
| 1-2 (Present Invention) | 87 |
| 1-3 (Present Invention) | 88 |
| 1-4 (Present Invention) | 86 |
| 1-5 (Present Invention) | 83 |
| 1-6 (Present Invention) | 85 |
| 1-7 (Comparison) | 72 |
| 1-8 (Comparison) | 23 |

It is apparent from the results shown in Table 3 that Samples 1—1 to 1-6 each containing the coupler according to the present invention are excellent in image fastness.

EXAMPLE 2

On a paper support, both surfaces of which were laminated with polyethylene, were coated layers as shown below in order to prepare a multilayer color printing paper which was designated Light-Sensitive Material 2-1. The coating solutions were prepared in the following manner. cl Preparation of Coating Solution for First Layer:

19.1 g of Yellow coupler (ExY) and 4.4 g of Color image stabilizer (Cpd-1) were dissolved in a mixture of 27.2 ml of ethyl acetate and 7.7 ml of Solvent (Solv-1) and the resulting solution was emulsified and dispersed in 185 ml of a 10% aqueous solution of gelatin containing 8 ml of a 10% aqueous solution of sodium dodecylbenzenesulfonate. Separately, to a silver chlorobromide emulsion (having a bromide content of 1.0 mol % and containing 70 g of silver per kg of the emulsion) was added $5.0 \times 10^{-4}$ mols of a blue-sensitive sensitizing dye shown below per mol of silver to prepare a blue-sensitive emulsion. The above described emulsified dispersion was mixed with the blue-sensitive silver chlorobromide emulsion, with the concentration of the resulting mixture being controlled, to form the composition shown below, i.e., the coating solution for the first layer.

Coating solutions for the second layer to the seventh layer were prepared in a similar manner as described for the coating solution for the first layer.

1-Oxy-3,5-dichloro-s-triazine sodium salt was used as a gelatin hardener in each layer.

The following spectral sensitizing dyes were employed in the emulsion layers, respectively.

Blue-Sensitive Emulsion Layer:

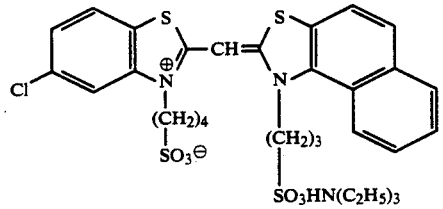

(Amount added: $6.0 \times 10^{-4}$ mol per mol of silver halide)

Green-Sensitive Emulsion Layer:

-continued

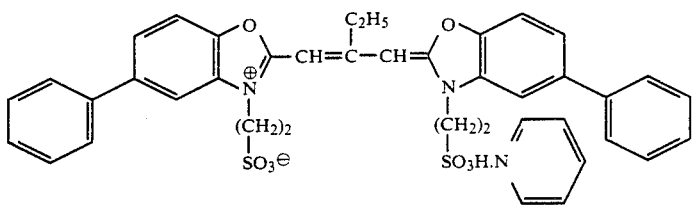

(Amount added: 4.0 × 10⁻⁴ mol per mol of silver halide)

and

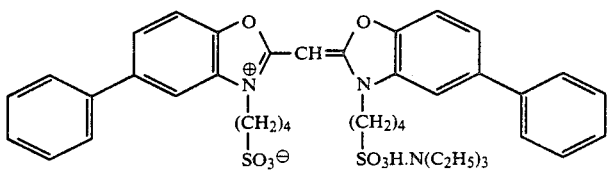

(Amount added: 8.0 × 10⁻⁵ mol per mol of silver halide)

Red-Sensitive Emulsion Layer:

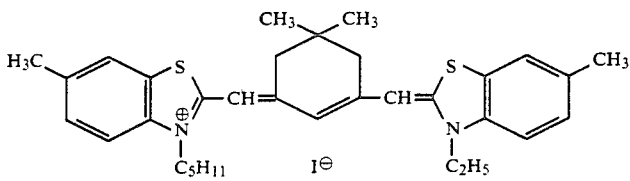

(Amount added: 1.8 × 10⁻⁴ mol per mol of silver halide)

To the red-sensitive emulsion layer, was added the compound shown below in an amount of $2.6 \times 10^{-3}$ mol per mol of silver halide.

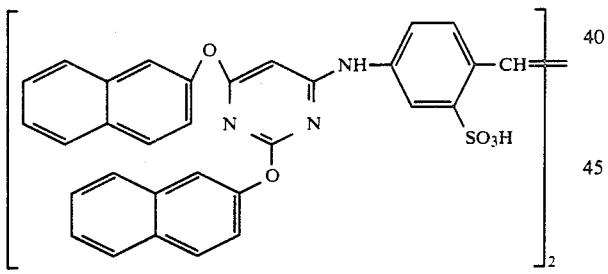

To the blue-sensitive emulsion layer, green-sensitive emulsion layer and red-sensitive emulsion layer, was added 8-(5-methylureidophenyl)-5-mercaptotetrazole in amount of $8.5 \times 10^{-5}$ mol, $7.7 \times 10^{-4}$ mol and $2.5 \times 10^{-4}$ mol per mol of silver halide, respectively.

Moreover, in order to prevent irradiation, the following dyes were added to the emulsion layers:

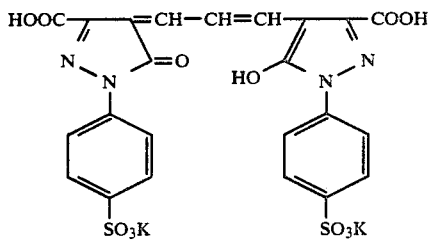

-continued
and

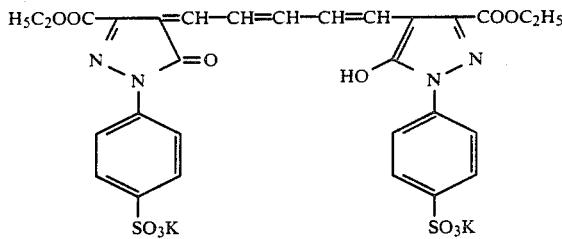

Layer Construction

The composition of each layer is shown below. The numerical values denote the coating amounts of components in g/m². The coating amount of silver halide emulsion is indicated in terms of silver coating amount.

| Support | Polyethylene laminated paper (the polyethylene coating containing a white pigment (TiO₂) and a bluish dye (ultramarine) on the first layer side) | |
|---|---|---|
| First Layer (Blue-sensitive layer) | Silver chlorobromide emulsion (Br: 1 mol %) | 0.30 |
| | Gelatin | 1.86 |
| | Yellow coupler (ExY) | 0.82 |
| | Color image stabilizer (Cpd-1) | 0.19 |
| | Solvent (Solv-1) | 0.35 |
| Second Layer (Color stain preventing layer) | Gelatin | 0.99 |
| | Color stain preventing agent (Cpd-2) | 0.08 |
| Third Layer | Silver chlorobromide | 0.36 |

| | | |
|---|---|---|
| (Green-sensitive layer) | emulsion (Br: 1 mol %) | |
| | Gelatin | 1.24 |
| | Magenta coupler (ExM) | 0.39 |
| | Color image stabilizer (Cpd-3) | 0.25 |
| | Color image stabilizer (Cpd-4) | 0.12 |
| | Solvent (Solv-2) | 0.25 |
| Fourth Layer (Ultraviolet light absorbing layer) | Gelatin | 1.60 |
| | Ultraviolet light absorbing agent (UV-1) | 0.70 |
| | Color stain preventing agent (Cpd-5) | 0.05 |
| | Solvent (Solv-3) | 0.42 |
| Fifth Layer (Red-sensitive layer) | Silver chlorobromide emulsion (Br: 1 mol %) | 0.23 |
| | Gelatin | 0.92 |
| | Cyan coupler (ExC) | 0.33 |

| | | |
|---|---|---|
| | Color image stabilizer (Cpd-6) | 0.17 |
| | Polymer (Cpd-7) | 0.14 |
| | Solvent (Solv-4) | 0.20 |
| Sixth Layer (Ultraviolet light absorbing layer) | Gelatin | 0.53 |
| | Ultraviolet light absorbing agent (UV-1) | 0.21 |
| | Solvent (Solv-3) | 0.08 |
| Seventh Layer (Protective layer) | Gelatin | 1.33 |
| | Acryl-modified polyvinyl alcohol copolymer (Degree of modification: 17%) | 0.17 |
| | Liquid paraffin | 0.03 |

The compounds used in the above-described layers have the structures shown below respectively:

Yellow coupler (ExY)

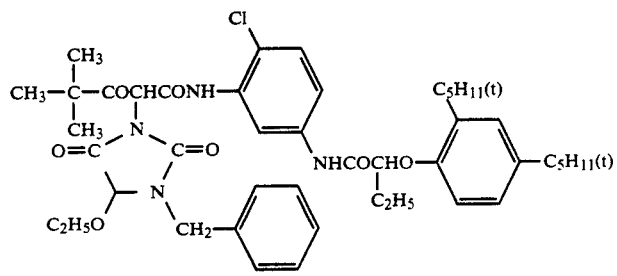

Magenta coupler (ExM)

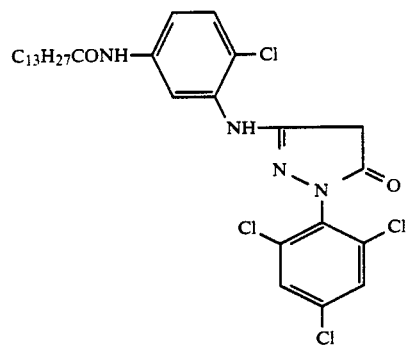

Cyan coupler (ExC) (corresponding to Compound (1))

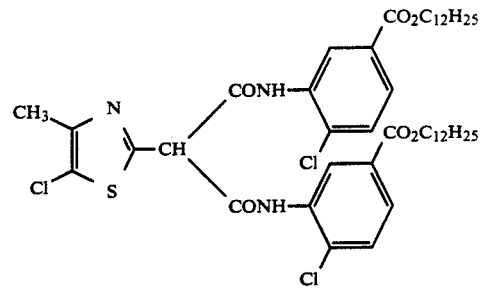

Color image stabilizer (Cpd-1)

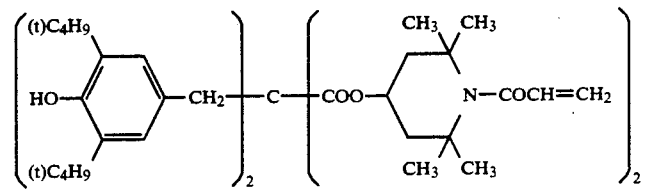

Color stain preventing agent (Cpd-2)
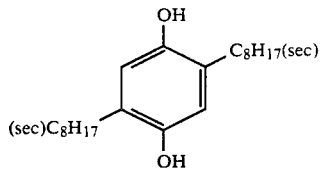
Color image stabilizer (Cpd-3)
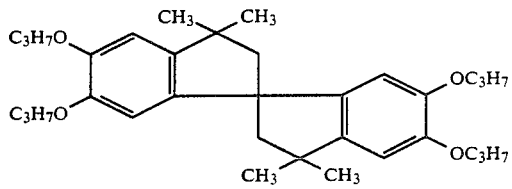
Color image stabilizer (Cpd-4)
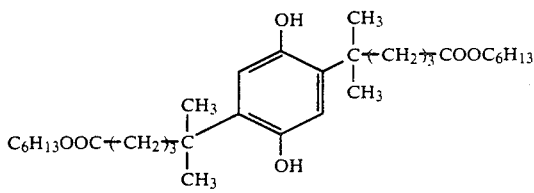
Color stain preventing agent (Cpd-5)
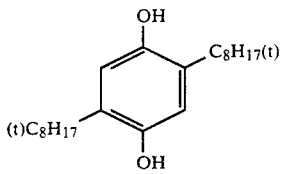
Color image stabilizer (Cpd-6)
A mixture of
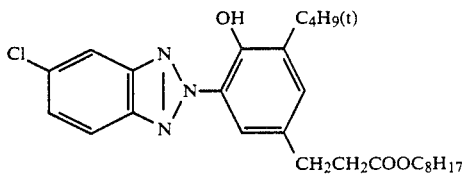
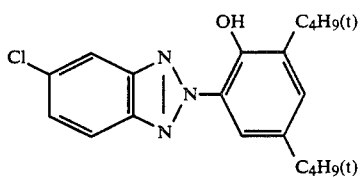
and
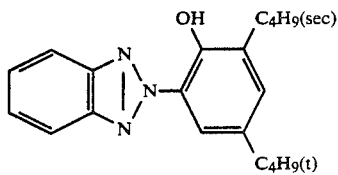
in a weight ratio of 5:8:9.
Polymer (Cpd-7)

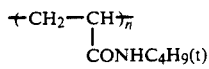

(average molecular weight: 80,000)

Ultraviolet light absorbing agent (UV-1)

A mixture of

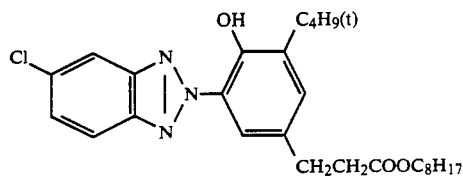

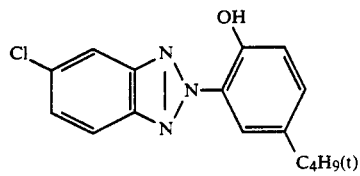

and

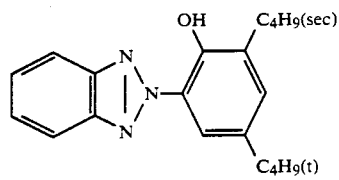

in a weight ratio of 2:9:8.

Solvent (Solv-1)

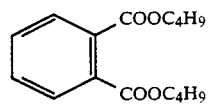

Solvent (Solv-2)

A mixture of

and

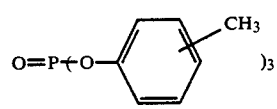

in a volume ratio of 1:1.

Solvent (Solv-3)

$O=P(O-C_9H_{19}\text{-iso})_3$

Solvent (Solv-4)

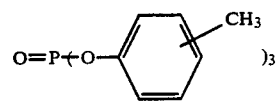

Light-Sensitive Materials 2—2 to 2-8 were prepared in the same manner as described for Light-Sensitive Material 2-1 except for using the equimolar amount of cyan couplers described in Table 4 below in the case of Light-Sensitive Materials 2—2 to 2-6 and 2-8, and 1.6 time molar amount of cyan coupler described in Table 4 below in the case of Light-Sensitive Material 2-7, in place of the cyan coupler employed in Light-Sensitive Material 2-1, respectively.

TABLE 4

| Light-Sensitive Material | Cyan Coupler | Remark |
| --- | --- | --- |
| 2-1 | (1) | Present Invention |
| 2-2 | (2) | " |
| 2-3 | (5) | " |
| 2-4 | (9) | " |
| 2-5 | (14) | " |
| 2-6 | (33) | " |
| 2-7 | Comparative Compound A* | Comparison |
| 2-8 | Comparative Compound B* | " |

*Comparative Compounds A and B were the same as those used in EXAMPLE 1.

Light-Sensitive Materials 2-1 to 2-8 thus-prepared were printed from a color negative film (Super HR 100 manufactured by Fuji Photo Film Co., Ltd.) which has been exposed to usual subjects and developed using a printer and then subjected to the development processing according to the following processing steps:

| Processing Step | Temperature (°C.) | Time |
| --- | --- | --- |
| Color Development | 35 | 45 sec. |
| Bleach-Fixing | 30 to 36 | 45 sec. |
| Stabilizing (1) | 30 to 37 | 20 sec. |
| Stabilizing (2) | 30 to 37 | 20 sec. |
| Stabilizing (3) | 30 to 37 | 20 sec. |
| Stabilizing (4) | 30 to 37 | 30 sec. |
| Drying | 70 to 85 | 60 sec. |

The stabilizing steps were conducted using a four-tank countercurrent system from Stabilizing (4) to Stabilizing (1).

The composition of each processing solution used was as follows:

| Color Developing Solution | |
| --- | --- |
| Water | 800 ml |
| Ethylenediaminetetraacetic acid | 2.0 g |
| Triethanolamine | 8.0 g |
| Sodium chloride | 1.4 g |
| Potassium carbonate | 25 g |
| N-Ethyl-N-(β-methanesulfonamidoethyl)-3-methyl-4-aminoaniline sulfate | 5.0 g |
| N,N-Diethylhydroxylamine | 4.2 g |
| 5,6-Dihydroxybenzene-1,2,4-trisulfonic acid | 0.3 g |
| Brightening agent (4,4'-diaminostilbene type) | 2.0 g |
| Water to make | 1000 ml |
| pH (25° C.) | 10.10 |
| Bleach-Fixing Solution | |
| Water | 400 ml |
| Ammonium thiosulfate (70% solution) | 100 ml |
| Sodium sulfite | 18 g |
| Ammonium ethylenediaminetetraacetato ferrate | 55 g |
| Disodium ethylenediaminetetraacetate | 3 g |
| Glacial acetic acid | 8 g |
| Water to make | 1,000 ml |
| pH (25° C.) | 5.5 |
| Stabilizing Solution | |
| Formalin (37%) | 0.1 g |
| Formalin-sulfite adduct | 0.7 g |
| 5-Chloro-2-methyl-4-isothiazolin-3-one | 0.02 g |
| 2-Methyl-4-isothiazolin-3-one | 0.01 g |
| Cupric sulfate | 0.005 g |
| Water to make | 1000 ml |
| pH (25° C.) | 4.0 |

After the development processing, each color print was cut into two parts, one part was stored under an ordinary condition and the other part was preserved at 60° C. and 70% of relative humidity for one month, in order to evaluate the image fastness thereof. As a result, with the prints obtained from Light-Sensitive Materials 2-1 to 2-6 almost no color fading was observed, although color fading of cyan image was clearly observed in the prints obtained from Light-Sensitive Materials 2-7 and 2-8.

EXAMPLE 3

On a paper support, both surfaces of which were laminated with polyethylene were coated a First Layer to a Twelfth Layer as shown below in order to prepare a multilayer color photographic light-sensitive material which was designated Light-Sensitive Material 3-1. The polyethylene coating on the First Layer side contained titanium white as a white pigment and a slight amount of ultramarine as a bluish dye.

Construction of Layers

The components and the coating amounts thereof in terms of g/m² are shown below. The coating amount of silver halide is indicated in terms of silver coating amount.

| | |
| --- | --- |
| First Layer: Gelatin Layer | |
| Gelatin | 1.30 |
| Second Layer: Antihalation Layer | |
| Black colloidal silver | 0.10 |
| Gelatin | 0.70 |
| Third Layer: Low-Speed Red-Sensitive Layer | |
| Silver iodobromide emulsion (silver iodide: 5.0 mol %; mean grain size: 0.4 μm) spectrally sensitized with Red sensitizing dyes (*1 and *2) | 0.15 |
| Gelatin | 1.00 |
| Cyan coupler (*3) | 0.19 |
| Discoloration inhibitor (*5, *6 and *7) | 0.10 |
| Coupler solvent (*8 and *9) | 0.06 |
| Fourth Layer: High-Speed Red-Sensitive Layer | |
| Silver iodobromide emulsion (silver iodide: 6.0 mol %; mean grain size: 0.7 μm) spectrally sensitized with Red sensitizing dyes (*1 and *2) | 0.15 |
| Gelatin | 1.00 |
| Cyan coupler (*3) | 0.27 |
| Discoloration inhibitor (*5, *6 and *7) | 0.15 |
| Coupler solvent (*8 and *9) | 0.10 |
| Fifth Layer: Intermediate Layer | |
| Magenta colloidal silver | 0.02 |

| | |
|---|---|
| Gelatin | 1.00 |
| Color stain preventing agent (*10) | 0.08 |
| Color stain preventing agent solvent (*11 and *12) | 0.16 |
| Polymer latex (*13) | 0.10 |
| Sixth Layer: Low-Speed Green-Sensitive Layer | |
| Silver iodobromide emulsion (silver iodide: 2.5 mol %; mean grain size: 0.4 μm) spectrally sensitized with Green sensitizing dye (*14) | 0.10 |
| Gelatin | 0.80 |
| Magenta coupler (*15) | 0.10 |
| Discoloration inhibitor (*16) | 0.10 |
| Stain preventing agent (*17) | 0.01 |
| Stain preventing agent (*18) | 0.001 |
| Coupler solvent (*11 and *19) | 0.15 |
| Seventh Layer: High-Speed Green-Sensitive Layer | |
| Silver iodobromide emulsion (silver iodide: 3.5 mol %; mean grain size: 0.9 μm) spectrally sensitized with Green sensitizing dye (*14) | 0.10 |
| Gelatin | 0.80 |
| Magenta coupler (*15) | 0.10 |
| Discoloration inhibitor (*16) | 0.10 |
| Stain preventing agent (*17) | 0.01 |
| Stain preventing agent (*18) | 0.001 |
| Coupler solvent (*11 and *19) | 0.15 |
| Eighth Layer: Yellow Filter Layer | |
| Yellow colloidal silver | 0.20 |
| Gelatin | 1.00 |
| Color stain preventing agent (*10) | 0.06 |
| Color stain preventing agent solvent (*11 and *12) | 0.15 |
| Polymer Latex (*13) | 0.10 |
| Ninth Layer: Low-Speed Blue-Sensitive Layer | |
| Silver iodobromide emulsion (silver iodide: 2.5 mol %; mean grain size: 0.5 μm) spectrally sensitized with Blue sensitizing dye (*20) | 0.15 |
| Gelatin | 0.50 |
| Yellow coupler (*21) | 0.20 |
| Stain preventing agent (*18) | 0.001 |
| Coupler solvent (*9) | 0.05 |
| Tenth Layer: High-Speed Blue-Sensitive Layer | |
| Silver iodobromide emulsion (silver iodide: 2.5 mol %; mean grain size: 1.2 μm) spectrally sensitized with Blue sensitizing dye (*20) | 0.25 |
| Gelatin | 1.00 |
| Yellow coupler (*21) | 0.40 |
| Stain preventing agent (*18) | 0.002 |
| Coupler solvent (*9) | 0.10 |
| Eleventh Layer: Ultraviolet Light Absorbing Layer | |
| Gelatin | 1.50 |
| Ultraviolet light absorbing agent (*22, *6 and *7) | 1.00 |
| Color stain preventing agent (*23) | 0.06 |
| Color stain preventing agent solvent (*9) | 0.15 |
| Anti-irradiation dye (*24) | 0.02 |
| Anti-irradiation dye (*25) | 0.02 |
| Twelfth Layer: Protective Layer | |
| Fine silver chlorobromide grains (silver chloride: 97 mol %, mean grain size, 0.2 μm) | 0.07 |
| Gelatin | 1.50 |
| Gelatin hardener (*26) | 0.17 |

*1 5,5'-Dichloro-3,3'-di(3-sulfobutyl)-9-ethylthiacarbocyanine sodium salt
*2 Triethylammonium 3-[2-{2-[3-(3-sulfopropyl)naphtho(1,2-d)thiazolin-2-indenemethyl]-1-butenyl}-3-naphtho(1,2-d)thiazolino]propanesulfonate
*3 Compound (1)
*5 2-(2-Hydroxy-3-sec-butyl-5-tert-butylphenyl)benzotriazole
*6 2-(2-Hydroxy-5-tert-butylphenyl)benzotriazole
*7 2-(2-Hydroxy-3,5-di-tert-butylphenyl)-6-chlorobenzotriazole
*8 Di(2-ethylhexyl) phthalate
*9 Trinonyl phosphate
*10 2,5-Di-tert-octylhydroquinone
*11 Tricresyl phosphate
*12 Dibutyl phthalate
*13 Polyethyl acrylate
*14 5,5'-Diphenyl-9-ethyl-3,3'-disulfopropyloxacarbocyanine sodium salt
*15 7-Chloro-6-methyl-2-[1-{2-octyloxy-5-(2-octyloxy-5-tert-octyl)benzenesulfonamido}-2-propyl]-1H-pyrazolo[1,5-b][1,2,4]triazole
*16 3,3,3',3'-Tetramethyl-5,6,5',6'-tetrapropoxy-1,1'-bisspiroindane
*17 3-(2-Ethylhexyloxycarbonyloxy)-1-(3-hexadecyloxyphenyl)-2-pyrazoline
*18 2-Methyl-5-tert-octylhydroquinone
*19 Trioctyl phosphate
*20 Triethylammonium 3-[2-(3-benzylrhodanin-5-ylidene)-3-benzoxazolynyl]propanesulfonate
*21 α-Pivaloyl-α-[(2,4-dioxo-1-benzyl-5-ethoxyhydantoin-3-yl]-2-chloro-5-(α-2,4-di-tert-amylphenoxy)butanamido]acetanilide
*22 5-Chloro-2-(2-hydroxy-3-tert-butyl-5-tert-octyl)phenylbenzotriazole
*23 2,5-Di-sec-octylhydroquinone

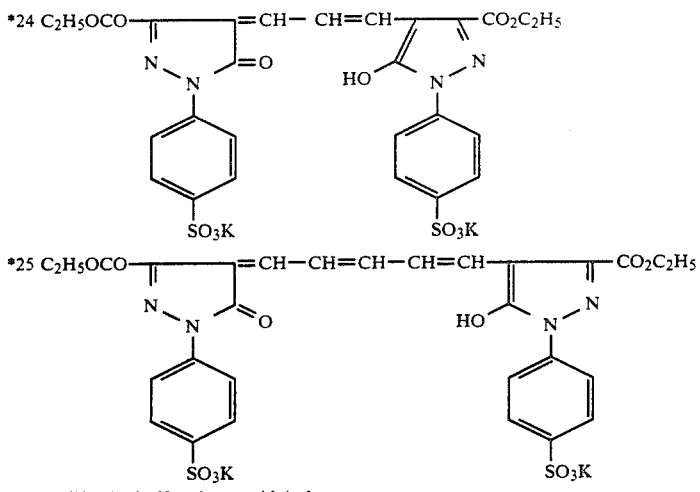

*26 1,2-Bis(vinylsulfonylacetamido)ethane

Light-Sensitive Materials 3-2 to 3-8 were prepared in the same manner as described for Light-Sensitive material 3-1 except for using the equimolar amounts of cyan couplers described in Table 5 below in place of the cyan coupler employed in Light-Sensitive Material 3-1, respectively.

TABLE 5

| Light-Sensitive Material | Cyan Coupler | Remark |
|---|---|---|
| 3-1 | (1) | Present Invention |
| 3-2 | (2) | " |
| 3-3 | (5) | " |
| 3-4 | (6) | " |
| 3-5 | (12) | " |
| 3-6 | (17) | " |
| 3-7 | (32) | " |
| 3-8 | Comparative Compound B* | Comparison |

*Comparative Compound B was the same as that used in EXAMPLE 1.

Light-Sensitive Materials 3-1 to 3-8 thus-prepared were printed from a color reversal film which has been exposed to usual subjects and developed using a printer and then subjected to development processing according to the following processing steps:

| Processing Steps | Time | Temperature (°C.) |
|---|---|---|
| First Development | 75 sec. | 38 |
| Washing with Water | 90 sec. | 33 |
| Reversal Exposure | 15 sec. | 100 lux (fluorescent lamp) |
| Color Development | 135 sec. | 38 |
| Second washing with Water | 45 sec. | 33 |
| Bleach-Fixing | 120 sec. | 38 |
| Washing with Water | 135 sec. | 33 |
| Drying | 45 sec. | 75 |

The processing solutions used had the following compositions.

| First Developing Solution: | |
|---|---|
| Pentasodium nitrilo-N,N,N-trimethylene-phosphonate | 1.0 g |
| Pentasodium diethylenetriamine-pentaacetate | 3.0 g |
| Potassium sulfite | 30.0 g |
| Potassium thiocyanate | 1.2 g |

| -continued | |
|---|---|
| First Developing Solution: | |
| Potassium carbonate | 35.0 g |
| Potassium hydroquinonemonosulfonate | 25.0 g |
| 1-Phenyl-4-hydroxymethyl-4-methyl-3-pyrazolidone | 2.0 g |
| Potassium bromide | 0.5 g |
| Potassium iodide | 5.0 mg |
| Water to make | 1,000 ml |
| | pH 9.60 |

The pH was adjusted with hydrochloric acid or potassium hydroxide.

| Color Developing Solution: | |
|---|---|
| Benzyl alcohol | 15.0 ml |
| Diethylene glycol | 12.0 ml |
| 3,6-Dithia-1,8-octanediol | 0.20 g |
| Pentasodium nitrilo-N,N,N-trimethylene-phosphonate | 0.5 g |
| Pentasodium diethylenetriaminepenta-acetate | 2.0 g |
| Sodium sulfite | 2.0 g |
| Hydroxylamine sulfate | 3.0 g |
| N-Ethyl-N-(β-methanesulfonamidoethyl)-3-methyl-4-aminoaniline sulfate | 5.0 g |
| Brightening agent (diaminostilbene type) | 1.0 g |
| Potassium bromide | 0.5 g |
| Potassium iodide | 1.0 mg |
| Water to make | 1,000 ml |
| | pH 10.25 |

The pH was adjusted with hydrochloric acid or potassium hydroxide.

| Bleach-Fixing Solution: | |
|---|---|
| Disodium ethylenediaminetetraacetate dihydrate | 5.0 g |
| Ammonium ethylenediaminetetraacetato ferrate monohydrate | 80.0 g |
| Sodium sulfite | 15.0 g |
| Ammonium thiosulfate (700 g/l-solution) | 160.0 ml |
| 2-Mercapto-1,3,4-triazole | 0.5 g |
| Water to make | 1,000 ml |
| | pH 6.50 |

The pH was adjusted with acetic acid or aqueous ammonia.

Washing Water and Second Washing Water

City water

As a result of the evaluation on image preservability of the reversal prints thus-obtained in the same manner as described in Example 2, it was found that the prints obtained from Light-Sensitive Materials 3-1 to 3-7 according to the present invention were excellent in image preservability.

EXAMPLE 4

On a cellulose triacetate film support provided with a subbing layer was coated each layer having the composition set forth below to prepare a multilayer color photographic light-sensitive material, which was designated Light-Sensitive Material 401.

With respect to the compositions of the layers, the coating amounts are shown in g/m$^2$, coating amounts of silver halide are shown in terms of silver coating amount in units of g/m$^2$, and those of sensitizing dyes are shown as a molar amount per mol of silver halide present in the same layer.

| First Layer: Antihalation Layer | |
|---|---|
| Black colloidal silver | 0.18 (as silver) |
| Gelatin | 0.40 |
| Second Layer: Intermediate Layer | |
| 2,5-Di-tert-pentadecylhydroquinone | 0.18 |
| EX-1 | 0.07 |
| EX-3 | 0.02 |
| EX-12 | 0.002 |
| U-1 | 0.06 |
| U-2 | 0.08 |
| U-3 | 0.10 |
| HBS-1 | 0.10 |
| HBS-2 | 0.02 |
| Gelatin | 1.04 |
| Third Layer: First Red-Sensitive Emulsion Layer | |
| Emulsion A | 0.25 (as silver) |
| Emulsion B | 0.25 (as silver) |
| Sensitizing Dye I | $6.9 \times 10^{-5}$ |
| Sensitizing Dye II | $1.8 \times 10^{-5}$ |
| Sensitizing Dye III | $3.1 \times 10^{-4}$ |
| EX-2 (Coupler (3) of the present invention) | 0.201 |
| EX-10 | 0.020 |
| Gelatin | 0.87 |
| Fourth Layer: Second Red-Sensitive Emulsion Layer | |
| Emulsion C | 1.0 (as silver) |
| Sensitizing Dye I | $5.1 \times 10^{-5}$ |
| Sensitizing Dye II | $1.4 \times 10^{-5}$ |
| Sensitizing Dye III | $2.3 \times 10^{-4}$ |
| EX-2 (Coupler (3) of the present invention) | 0.240 |
| EX-3 | 0.050 |
| EX-10 | 0.015 |
| Gelatin | 1.30 |
| Fifth Layer: Third Red-Sensitive Emulsion Layer | |
| Emulsion D | 1.60 (as silver) |
| Sensitizing Dye I | $5.4 \times 10^{-5}$ |
| Sensitizing Dye II | $1.4 \times 10^{-5}$ |
| Sensitizing Dye III | $2.4 \times 10^{-4}$ |
| EX-3 | 0.010 |
| EX-4 | 0.080 |
| EX-2 (Coupler (3) of the present invention) | 0.058 |
| HBS-1 | 0.22 |
| HBS-2 | 0.10 |
| Gelatin | 1.63 |
| Sixth Layer: Intermediate Layer | |
| EX-5 | 0.040 |
| HBS-1 | 0.020 |
| Gelatin | 0.80 |
| Seventh Layer: First Green-Sensitive Emulsion Layer | |
| Emulsion A | 0.15 (as silver) |
| Emulsion B | 0.15 (as silver) |
| Sensitizing Dye V | $3.0 \times 10^{-5}$ |
| Sensitizing Dye VI | $1.0 \times 10^{-4}$ |
| Sensitizing Dye VII | $3.8 \times 10^{-4}$ |
| EX-6 | 0.260 |
| EX-1 | 0.021 |
| EX-7 | 0.030 |
| EX-8 | 0.025 |
| HBS-1 | 0.100 |
| HBS-3 | 0.010 |
| Gelatin | 0.63 |
| Eighth Layer: Second Green-Sensitive Emulsion Layer | |
| Emulsion C | 0.45 (as silver) |
| Sensitizing Dye V | $2.1 \times 10^{-5}$ |
| Sensitizing Dye VI | $7.0 \times 10^{-5}$ |
| Sensitizing Dye VII | $2.6 \times 10^{-4}$ |
| EX-6 | 0.094 |
| EX-8 | 0.018 |
| EX-7 | 0.026 |
| HBS-1 | 0.160 |
| HBS-3 | 0.008 |
| Gelatin | 0.50 |
| Ninth Layer: Third Green-Sensitive Emulsion Layer | |
| Emulsion E | 1.2 (as silver) |
| Sensitizing Dye V | $3.5 \times 10^{-5}$ |
| Sensitizing Dye VI | $8.0 \times 10^{-5}$ |
| Sensitizing Dye VII | $3.0 \times 10^{-4}$ |
| EX-13 | 0.015 |
| EX-11 | 0.100 |
| EX-1 | 0.025 |
| HBS-1 | 0.25 |
| HBS-2 | 0.10 |
| Gelatin | 1.54 |
| Tenth Layer: Yellow Filter Layer | |
| Yellow Colloidal Silver | 0.05 (as silver) |
| EX-5 | 0.08 |
| HBS-1 | 0.03 |
| Gelatin | 0.95 |
| Eleventh Layer: First Blue-Sensitive Emulsion Layer | |
| Emulsion A | 0.08 (as silver) |
| Emulsion B | 0.07 (as silver) |
| Emulsion F | 0.07 (as silver) |
| Sensitizing Dye VIII | $3.5 \times 10^{-4}$ |
| EX-9 | 0.721 |
| EX-8 | 0.042 |
| HBS-1 | 0.28 |
| Gelatin | 1.10 |
| Twelfth Layer: Second Blue-Sensitive Emulsion Layer | |
| Emulsion G | 0.45 (as silver) |
| Sensitizing Dye VIII | $2.1 \times 10^{-4}$ |
| EX-9 | 0.154 |
| EX-10 | 0.007 |
| HBS-1 | 0.05 |
| Gelatin | 0.78 |
| Thirteenth Layer: Third Blue-Sensitive Emulsion Layer | |
| Emulsion H | 0.77 (as silver) |
| Sensitizing Dye VIII | $2.2 \times 10^{-4}$ |
| EX-9 | 0.20 |

| | -continued | |
|---|---|---|
| HBS-1 | | 0.07 |
| Gelatin | | 0.69 |
| Fourteenth Layer: First Protective Layer | | |
| Emulsion I | | 0.5 |
| | | (as silver) |
| U-4 | | 0.11 |
| U-5 | | 0.17 |
| HBS-1 | | 0.05 |
| Gelatin | | 1.00 |
| Fifteenth Layer: Second Protective Layer | | |

| | -continued | |
|---|---|---|
| Polymethyl methacrylate particle (diameter: about 1.5 μm) | | 0.54 |
| S-1 | | 0.20 |
| Gelatin | | 1.20 |

Gelatin Hardener H-1 and a surface active agent were added to each of the layers of addition to the above described components.

The components employed for the preparation of Light-Sensitive Material 401 are shown below.

| Emulsion | Average AgI Content (%) | Average Particle Diameter (μm) | Coefficient of Variation on Particle Diameter (%) | Diameter/ Thickness Ratio | Ratio of Silver Amount (AgI Content %) |
|---|---|---|---|---|---|
| A | 4.3 | 0.45 | 27 | 1 | Triple Structure Grain Core/Middle/Shell = 8/16/76 (0/27/0) |
| B | 8.7 | 0.70 | 14 | 1 | Triple Structure Grain Core/Middle/Shell = 8/16/76 (0/27/0) |
| C | 10 | 0.75 | 30 | 2 | Double Structure Grain Core/Shell = 1/2 (24/3) |
| D | 16 | 1.05 | 35 | 2 | Double Structure Grain Core/Shell = 1/2 (40/0) |
| E | 10 | 1.05 | 35 | 3 | Double Structure Grain Core/Shell = 1/2 (24/3) |
| F | 4.3 | 0.25 | 28 | 1 | Triple Structure Grain Core/Middle/Shell = 8/16/76 (0/27/0) |
| G | 14 | 0.75 | 25 | 2 | Double Structure Grain Core/Shell = 1/2 (40/0) |
| H | 14 | 1.30 | 25 | 2 | Double Structure Grain Core/Shell = 1/2 (24/3) |
| I | 1 | 0.07 | 15 | 1 | |

EX-1

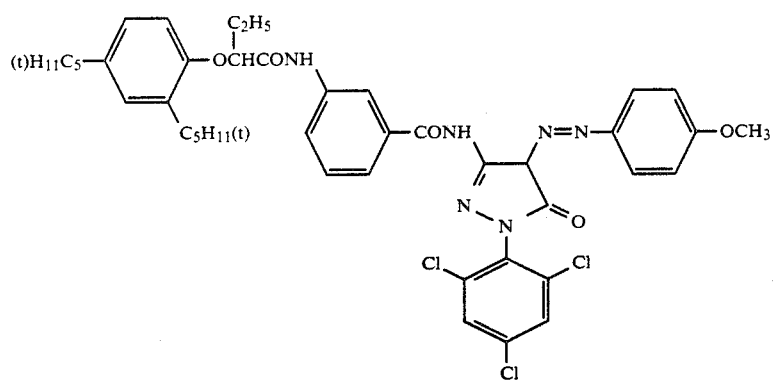

EX-2 (corresponding to Compound (3) of the present invention)

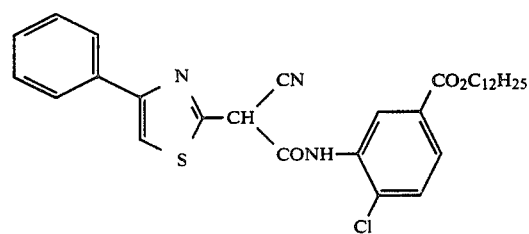

EX-3

-continued
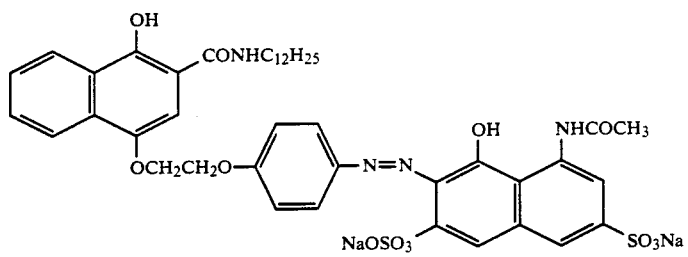
EX-4
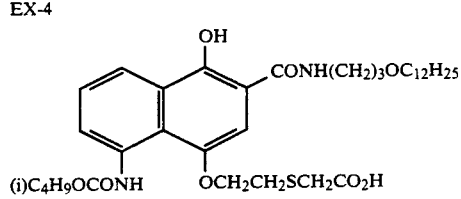
EX-5
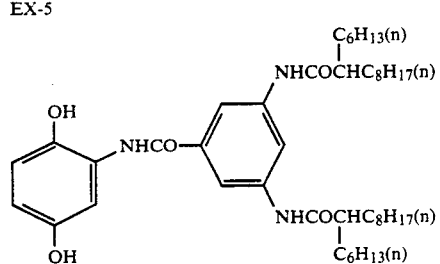
EX-6
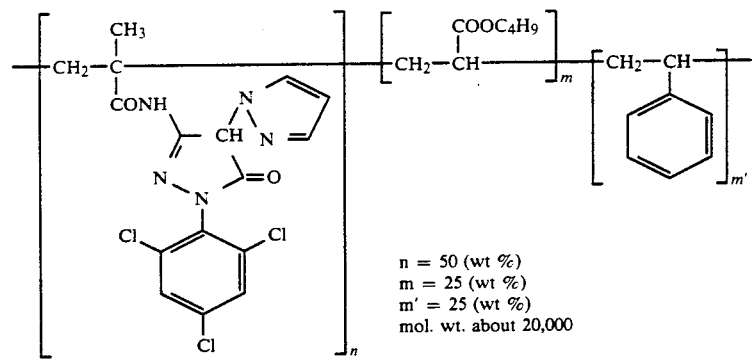
n = 50 (wt %)
m = 25 (wt %)
m' = 25 (wt %)
mol. wt. about 20,000
EX-7
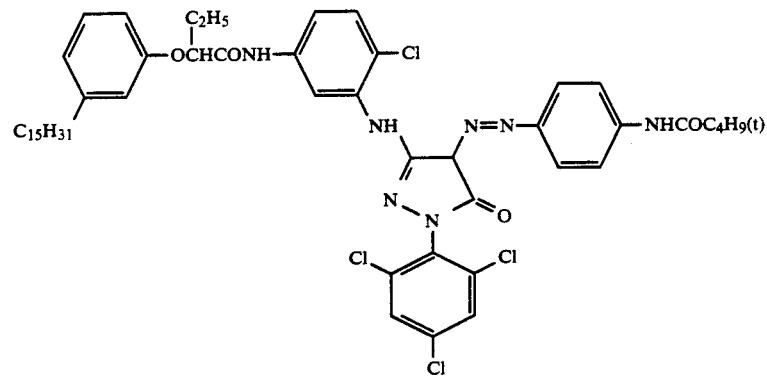
EX-8

-continued
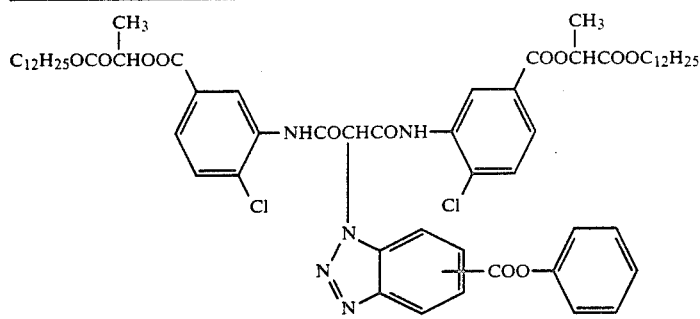
EX-9
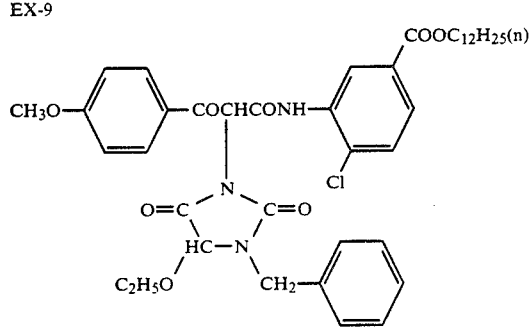
EX-10
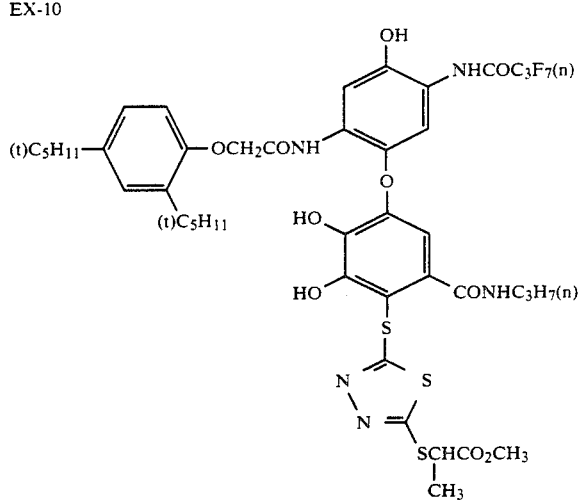
EX-11
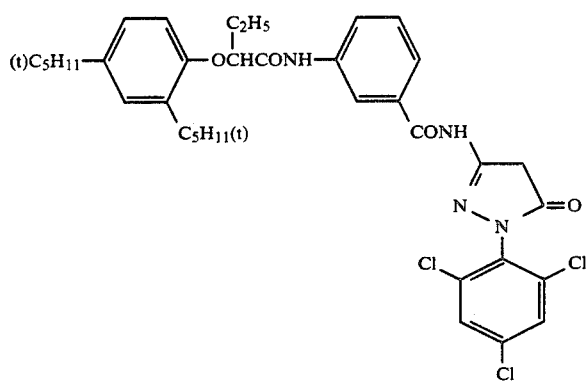
EX-12

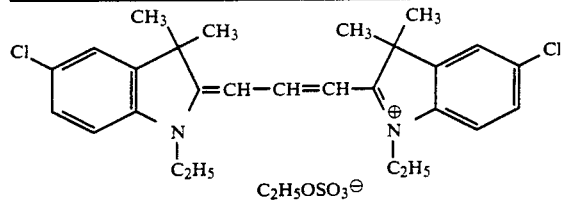
EX-13
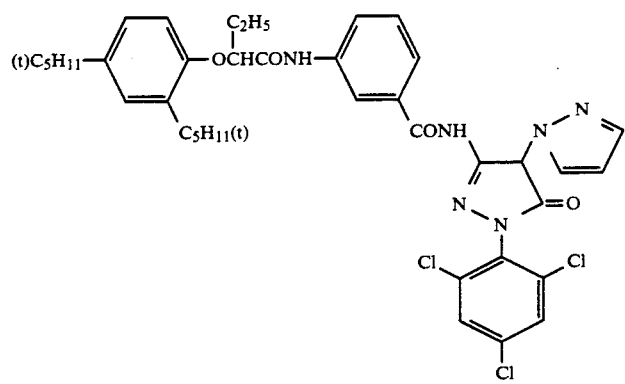
U-1
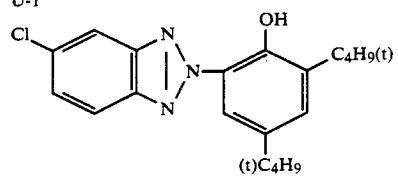
U-2
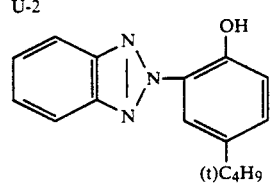
U-3
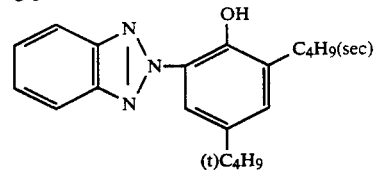
U-4
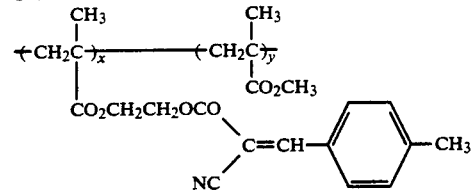
x:y = 70:30 (wt %)
mol. wt. average 30,000
UV-5
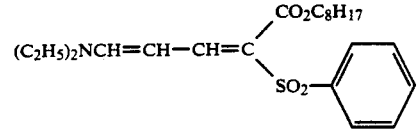

-continued
HBS-1 Tricresyl phosphate
HBS-2 Di-n-butylphthalate
HBS-3
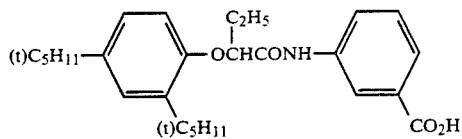
Sensitizing Dye I
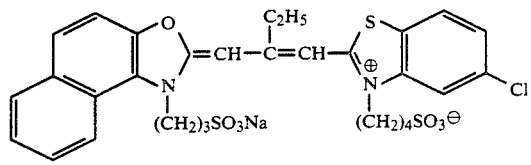
Sensitizing Dye II
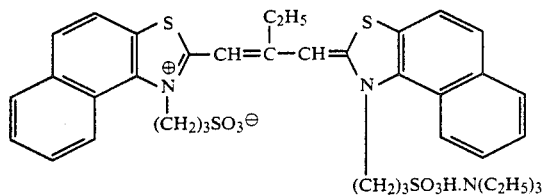
Sensitizing Dye III
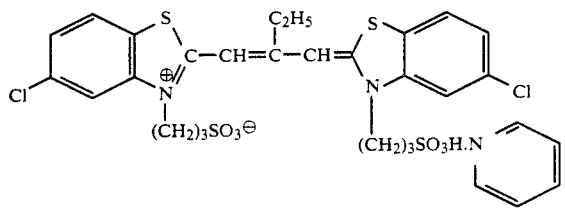
Sensitizing Dye V
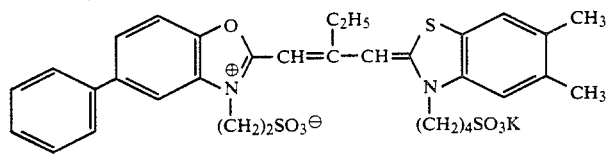
Sensitizing Dye VI
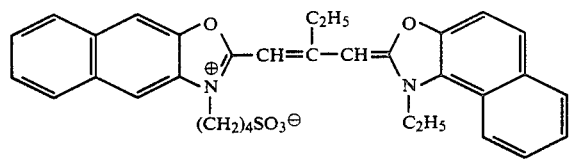
Sensitizing Dye VII
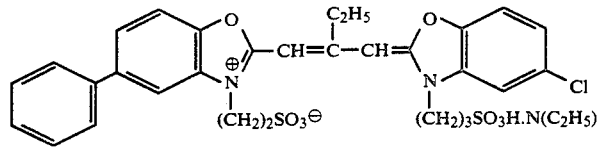
Sensitizing Dye VIII
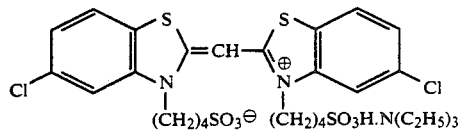

S-1
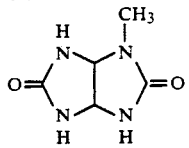

H-1
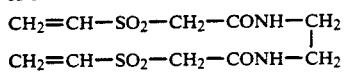

Light-Sensitive Materials 402 to 407 were prepared in the same manner as described for Light-Sensitive Material 401 except for using the equimolar amount of cyan couplers described in Table 6 below in the case of Light-Sensitive Materials 402 to 406, and 1.6 time molar amounts of cyan coupler described in Table 6 below in the case of Light-Sensitive Material 407, in place of the cyan coupler EX-2 (compound (3) of the present invention) used in the third layer, fourth layer and fifth layer of Light-Sensitive Material 401, respectively.

TABLE 6

| Light-Sensitive Material | Cyan Coupler Used in Third Layer, Fourth Layer and Fifth Layer | Remark |
| --- | --- | --- |
| 401 | (3) | Present Invention |
| 402 | (7) | " |
| 403 | (8) | " |
| 404 | (11) | " |
| 405 | (16) | " |
| 406 | (18) | " |
| 407 | Comparative Compound E | Comparison |

Comparative Compound E (conventional type cyan coupler)

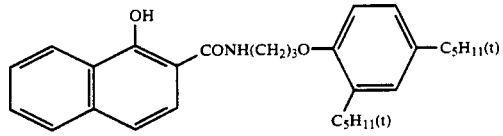

Light-Sensitive Materials 401 to 407 thus-prepared were cut into a 35 m/m width strip, photographed with usual subjects and then subjected to development processing according to the following processing steps:

| Processing Step | Processing Time | Processing Temperature (°C.) |
| --- | --- | --- |
| Color Development | 3 min. 15 sec. | 38 |
| Bleaching | 1 min. 00 sec. | 38 |
| Bleach-Fixing | 3 min. 15 sec. | 38 |
| Washing with Water (1) | 40 sec. | 35 |
| Washing with Water (2) | 1 min. 00 sec. | 35 |
| Stabilizing | 40 sec. | 38 |
| Drying | 1 min. 15 sec. | 55 |

The composition of each processing solution used is illustrated below.

| Color Developing Solution: | |
| --- | --- |
| Diethylenetriaminepentaacetic acid | 1.0 g |
| 1-Hydroxyethylidene-1,1-diphosphonic acid | 3.0 g |
| Sodium sulfite | 4.0 g |
| Potassium carbonate | 30.0 g |
| Potassium bromide | 1.4 g |
| Potassium iodide | 1.5 mg |
| Hydroxylamine sulfate | 2.4 g |
| 4-(N-Ethyl-N-β-hydroxyethylamino)-2-methylaniline sulfate | 4.5 g |
| Water to make | 1.0 l |
| pH | 10.05 |
| Bleaching Solution: | |
| Ammonium ethylenediaminetetraacetato ferrate dihydrate | 120.0 g |
| Disodium ethylenediaminetetraacetate | 10.0 g |
| Ammonium bromide | 100.0 g |
| Ammonium nitrate | 10.0 g |
| Bleach accelerating agent | 0.005 mol |

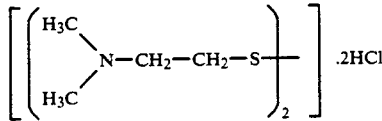

| Aqueous ammonia (27%) | 15.0 ml |
| --- | --- |
| Water to make | 1.0 l |
| pH | 6.3 |
| Bleach-Fixing Solution: | |
| Ammonium ethylenediaminetetraacetato ferrate dihydrate | 50.0 g |
| Disodium ethylenediaminetetraacetate | 5.0 g |
| Sodium sulfite | 12.0 g |
| Aqueous solution of ammonium thiosulfate (70%) | 240.0 ml |
| Aqueous ammonia (27%) | 6.0 ml |
| Water to make | 1.0 l |
| pH | 7.2 |

Washing Water

City water was passed through a mixed bed type column filled with an H type strong acidic cation exchange resin (Amberlite IR-120B manufactured by Rohm & Haas Co.) and an OH type strong basic anion exchange resin (Amberlite IRA-400 manufactured by Rohm & Haas Co.) to prepare water containing not more than 3 mg/l of calcium ion and magnesium ion. To the water thus-treated were added sodium dichloroisocyanulate in an amount of 20 mg/l and sodium sulfate in an amount of 0.15 g/l. The pH of the solution was in a range from 6.5 to 7.5.

| Stabilizing Solution: | |
| --- | --- |
| Formalin (37%) | 2.0 ml |
| Polyoxyethylene-p-monononylphenylether (average degree of polymerization: 10) | 0.3 g |
| Disodium ethylenediaminetetraacetate | 0.05 g |
| Water to make | 1.0 l |
| pH | 5.0 to 8.0 |

Each of the color negative films thus-obtained was printed to color paper using a color printer, and the color paper were subjected to standard development processing to prepare color prints. As a result, it was found that the color prints obtained from the negative films of Light-Sensitive Materials 401 to 406 according to the present invention were excellent in sharpness as compared with the color print obtained from the negative film of Light-Sensitive Material 407. This is based on the reduction in thickness of emulsion layer which can be attained by using a small amount of the cyan coupler according to the present invention for obtaining sufficiently high image density.

EXAMPLE 5

On a cellulose triacetate film support provided with a subbing layer was coated each layer having the composition set forth below to prepare a multilayer color photographic light-sensitive material which was designated Light-Sensitive Material 501.

With respect to the compositions of the layers, coating amounts of silver halide and colloidal silver are shown by g/m² units in terms of silver, the coating amounts of couplers, additives and gelatin are shown by g/m² units, and the coating amounts of sensitizing dyes are shown by mol number per mol of silver halide present in the same layer.

The symbols which denote additives used below have the meanings described in the following. When the additive has two or more functions, one of them is indicated as the representative.

| | |
|---|---|
| UV: | Ultraviolet light absorbing agent |
| Solv: | Organic solvent having a high boiling point |
| ExF: | Dye |
| ExS: | Sensitizing dye |
| ExC: | Cyan coupler |
| ExM: | Magenta coupler |
| ExY: | Yellow coupler |
| Cpd: | Additive |

First Layer: Antihalation Layer

| | |
|---|---|
| Black colloidal silver | 0.15 |
| Gelatin | 2.9 |
| UV-1 | 0.03 |
| UV-2 | 0.06 |
| UV-3 | 0.07 |
| Solv-2 | 0.08 |
| ExF-1 | 0.01 |
| ExF-2 | 0.01 |

Second Layer: Low-Speed Red-Sensitive Emulsion Layer

| | |
|---|---|
| Silver iodobromide emulsion (AgI: 4 mol %, uniform AgI type, diameter corresponding to sphere: 0.4 μm, coefficient of variation of diameter corresponding to sphere: 37%, tabular grain, diameter/thickness ratio: 3.0) | 0.4 (as silver) |
| Gelatin | 0.8 |
| ExS-1 | $2.3 \times 10^{-4}$ |
| ExS-2 | $1.4 \times 10^{-4}$ |
| ExS-5 | $2.3 \times 10^{-4}$ |
| ExS-7 | $8.0 \times 10^{-6}$ |
| Compound (8) of the present invention | 0.13 |
| ExC-2 | 0.03 |
| ExC-3 | 0.13 |

Third Layer: Medium-Speed Red-Sensitive Emulsion Layer

| | |
|---|---|
| Silver iodobromide emulsion (AgI: 6 mol %, internal high AgI type, with core/shell ratio of 2:1, diameter corresponding to sphere: 0.65 μm, coefficient of variation of diameter corresponding to sphere: 25%, tabular grain, diameter/thickness ratio: 2.0) | 0.65 (as silver) |
| Silver iodobromide emulsion (AgI: 4 mol %, uniform AgI type, diameter corresponding to sphere: 0.4 μm, coefficient of variation of diameter corresponding to sphere: 37%, tabular grain, diameter/thickness ratio: 3.0) | 0.1 (as silver) |
| Gelatin | 1.0 |
| ExS-1 | $2 \times 10^{-4}$ |
| ExS-2 | $1.2 \times 10^{-4}$ |
| ExS-5 | $2 \times 10^{-4}$ |
| ExS-7 | $7 \times 10^{-6}$ |
| ExC-1 | 0.31 |
| Compound (14) of the present invention | 0.01 |
| ExC-3 | 0.06 |

Fourth Layer: High-Speed Red-sensitive Emulsion Layer

| | |
|---|---|
| Silver iodobromide emulsion (AgI: 6 mol %, internal high AgI type, with core/shell ratio of 2:1, diameter corresponding to sphere: 0.7 μm, coefficient of variation of diameter corresponding to sphere: 25%, tabular grain, diameter/thickness ratio: 2.5) | 0.9 (as silver) |
| Gelatin | 0.8 |
| ExS-1 | $1.6 \times 10^{-4}$ |
| ExS-2 | $1.6 \times 10^{-4}$ |
| Exs-5 | $1.6 \times 10^{-4}$ |
| ExS-7 | $6 \times 10^{-4}$ |
| ExC-1 | 0.07 |
| ExC-4 | 0.05 |
| Solv-1 | 0.07 |
| Solv-2 | 0.20 |
| Cpd-7 | $4.6 \times 10^{-4}$ |

Fifth Layer: Intermediate Layer

| | |
|---|---|
| Gelatin | 0.6 |
| UV-4 | 0.03 |
| UV-5 | 0.04 |
| Cpd 1 | 0.1 |
| Polyethyl acrylate latex | 0.08 |
| Solv-1 | 0.05 |

Sixth Layer: Low-Speed Green-Sensitive Emulsion Layer

| | |
|---|---|
| Silver iodobromide emulsion (AgI: 4 mol %, uniform AgI type, diameter corresponding to sphere: 0.4 μm, coefficient of variation of diameter corresponding to sphere: 37%, tabular grain, diameter/thickness ratio: 2.0) | 0.18 (as silver) |
| Gelatin | 0.4 |
| ExS-3 | $2 \times 10^{-4}$ |
| ExS-4 | $7 \times 10^{-4}$ |
| ExS-5 | $1 \times 10^{-4}$ |
| ExM-5 | 0.11 |
| ExM-7 | 0.03 |
| ExY-8 | 0.01 |
| Solv-1 | 0.09 |
| Solv-4 | 0.01 |

Seventh Layer: Medium-Speed Green-Sensitive Emulsion Layer

| | |
|---|---|
| Silver iodobromide emulsion (AgI: 4 mol %, surface high AgI type, with core/shell ratio of 1:1, diameter corresponding to sphere: 0.5 μm, coefficient of variation of diameter corresponding to sphere: 20%, tabular grain, diameter/thickness ratio: 4.0) | 0.27 (as silver) |
| Gelatin | 0.6 |
| ExS-3 | $2 \times 10^{-4}$ |
| ExS-4 | $7 \times 10^{-4}$ |
| ExS-5 | $1 \times 10^{-4}$ |
| ExM-5 | 0.17 |
| ExM-7 | 0.04 |
| ExY-8 | 0.02 |
| Solv-1 | 0.14 |
| Solv-4 | 0.02 |

-continued

Eighth Layer: High-Speed Green-Sensitive Emulsion Layer

| | |
|---|---|
| Silver iodobromide emulsion (AgI: 8.7 mol %, multi-layer structure grain having silver amount of 3:4:2, AgI content: 24 mol, 0 mol, 3 mol from inside, diameter corresponding to sphere: 0.7 μm, coefficient of variation of diameter corresponding to sphere 25%, tabular grain, diameter/thickness ratio: 1.6) | 0.7 (as silver) |
| Gelatin | 0.8 |
| ExS-4 | $5.2 \times 10^{-4}$ |
| ExS-5 | $1 \times 10^{-4}$ |
| ExS-8 | $0.3 \times 10^{-4}$ |
| ExM-5 | 0.1 |
| ExM-6 | 0.03 |
| ExY-8 | 0.02 |
| ExC-1 | 0.02 |
| ExC-4 | 0.01 |
| Solv-1 | 0.25 |
| Solv-2 | 0.06 |
| Solv-4 | 0.01 |
| Cpd-7 | $1 \times 10^{-4}$ |

Ninth Layer: Intermediate Layer

| | |
|---|---|
| Gelatin | 0.6 |
| Cpd-1 | 0.04 |
| Polyethyl acrylate latex | 0.12 |
| Solv-1 | 0.02 |

Tenth Layer: Donor Layer of Interimage Effect to Red-Sensitive Layer

| | |
|---|---|
| Silver iodobromide emulsion (AgI: 6 mol %, internal high AgI type, with core/shell ratio of 2:1, diameter corresponding to sphere: 0.7 μm, coefficient of variation of diameter corresponding to sphere: 25%, tabular grain, diameter/thickness ratio: 2.0) | 0.68 (as silver) |
| Silver iodobromide emulsion (AgI: 4 mol %, uniform AgI type, diameter corresponding to sphere: 0.4 μm, coefficient of variation of diameter corresponding to sphere: 37%, tabular grain, diameter/thickness ratio: 3.0) | 0.19 (as silver) |
| Gelatin | 1.0 |
| ExS-3 | $6 \times 10^{-4}$ |
| ExM-10 | 0.19 |
| Solv-1 | 0.20 |

Eleventh Layer: Yellow Filter Layer

| | |
|---|---|
| Yellow Colloidal Silver | 0.06 |
| Gelatin | 0.8 |
| Cpd-2 | 0.13 |
| Solv-1 | 0.13 |
| Cpd-1 | 0.07 |
| Cpd-6 | 0.002 |
| H-1 | 0.13 |

Twelfth Layer: Low-Speed Blue-sensitive Emulsion Layer

| | |
|---|---|
| Silver iodobromide emulsion (AgI: 4.5 mol %, uniform AgI type, diameter corresponding to sphere: 0.7 μm, coefficient of variation of diameter corresponding to sphere: 15%, tabular grain, diameter/thickness ratio: 7.0) | 0.3 (as silver) |
| Silver iodobromide emulsion (AgI: 3 mol %, uniform AgI type, diameter corresponding to sphere: 0.3 μm, coefficient of variation of diameter corresponding to sphere: 30%, tabular grain, diameter/thickness ratio: 7.0) | 0.15 (as silver) |
| Gelatin | 1.8 |
| ExS-6 | $9 \times 10^{-4}$ |
| ExC-1 | 0.06 |
| ExC-4 | 0.03 |
| ExY-9 | 0.14 |
| ExY-11 | 0.89 |
| Solv-1 | 0.42 |

Thirteenth Layer: Intermediate Layer

| | |
|---|---|
| Gelatin | 0.7 |
| ExY-12 | 0.20 |
| Solv-1 | 0.34 |

Fourteenth Layer: High-Speed Blue-sensitive Emulsion Layer

| | |
|---|---|
| Silver iodobromide emulsion (AgI: 10 mol %, internal high AgI type, diameter corresponding to sphere: 1.0 μm, coefficient of variation of diameter corresponding to sphere: 25%, multiple twin tabular grain, diameter/thickness ratio: 2.0) | 0.5 (as silver) |
| Gelatin | 0.5 |
| ExS-6 | $1 \times 10^{-4}$ |
| ExY-9 | 0.01 |
| ExY-11 | 0.20 |
| ExC-1 | 0.02 |
| Solv-1 | 0.10 |

Fifteenth Layer: First Protective Layer

| | |
|---|---|
| Fine grain silver iodobromide emulsion (AgI: 2 mol %, uniform AgI type, diameter corresponding to sphere: 0.07 μm) | 0.12 (as silver) |
| Gelatin | 0.9 |
| UV-4 | 0.11 |
| UV-5 | 0.16 |
| Solv-5 | 0.02 |
| H-1 | 0.13 |
| Cpd-5 | 0.10 |
| Polyethyl acrylate latex | 0.09 |

Sixteenth Layer: Second Protective Layer

| | |
|---|---|
| Fine grain silver iodobromide emulsion (AgI: 2 mol %, uniform AgI type, diameter corresponding to sphere: 0.07 μm) | 0.36 (as silver) |
| Gelatin | 0.55 |
| Polymethyl methacrylate particle (diameter: 1.5 μm) | 0.2 |
| H-1 | 0.17 |

Each layer described above further contained a stabilizer for emulsion (Cpd-3: 0.07 g/m²) and a surface active agent (Cpd-4: 0.03 g/m²) as a coating aid in addition to the above-described compounds.

The compounds used for the preparation of the light-sensitive material are illustrated below.

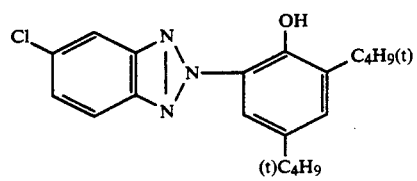

UV-1

-continued
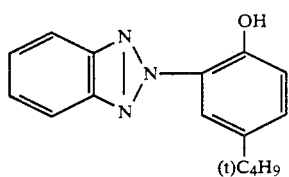 UV-2
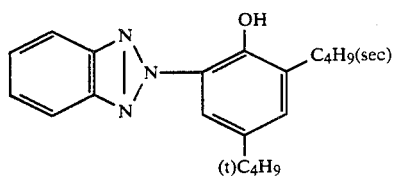 UV-3
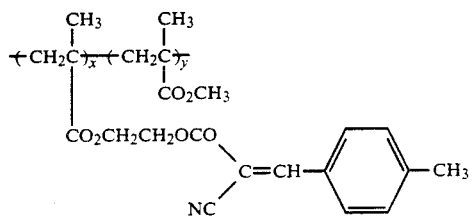 UV-4
x:y = 70:30 (wt %)
mol. wt. average 30,000
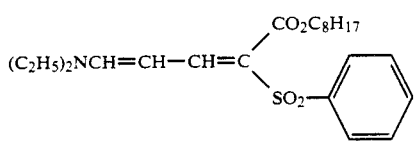 (UV-5
Tricresyl phosphate — Solv-1
Dibutyl phthalate — Solv-2
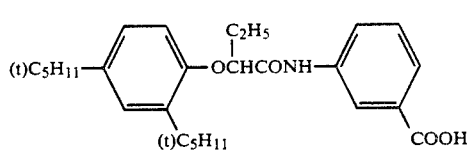 Solv-4
Trihexyl phosphate — Solv-5
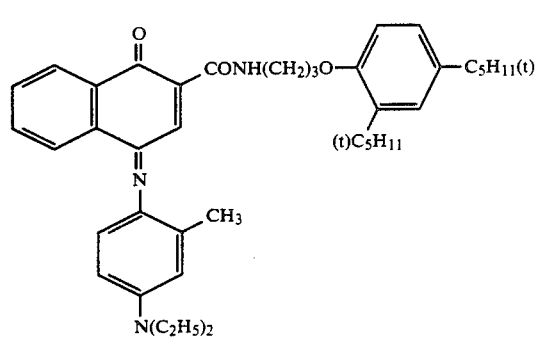 ExF-1

ExF-2
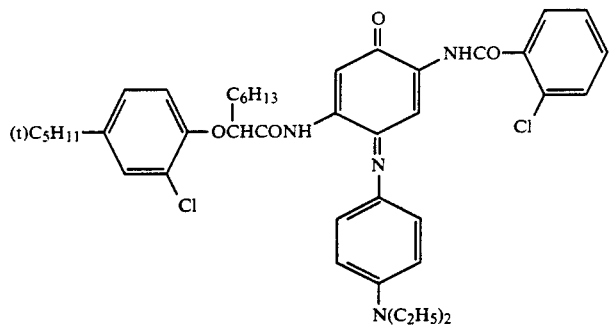
ExS-1
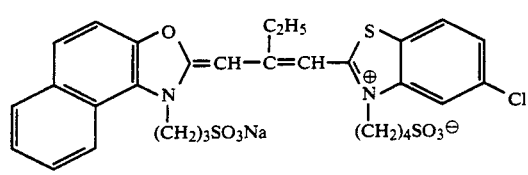
ExS-2
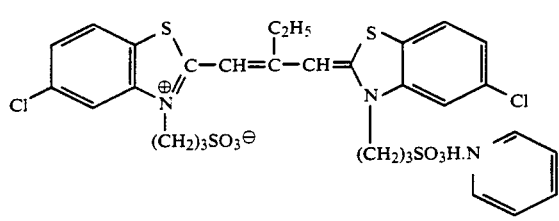
ExS-3
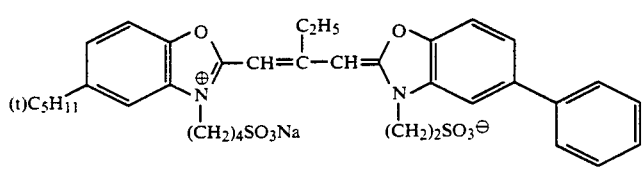
ExS-4
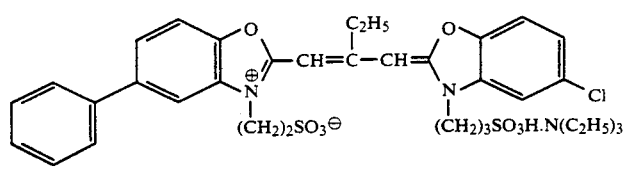
ExS-5
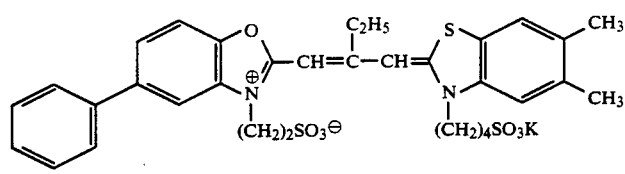
ExS-6
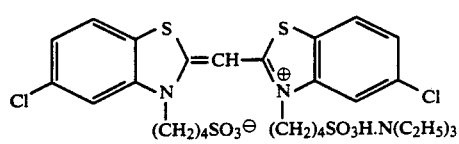
ExS-7
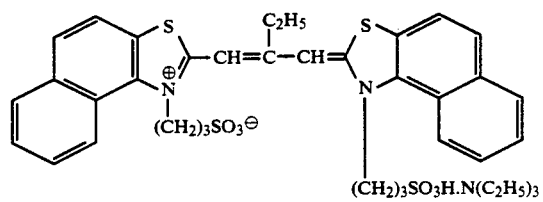

-continued
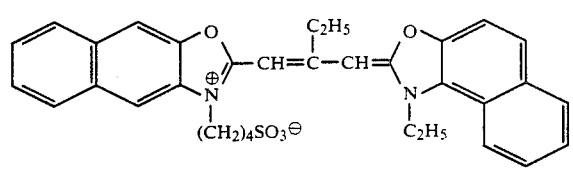
ExS-8
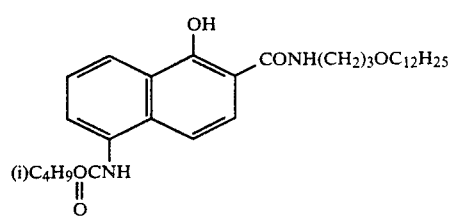
ExC-1
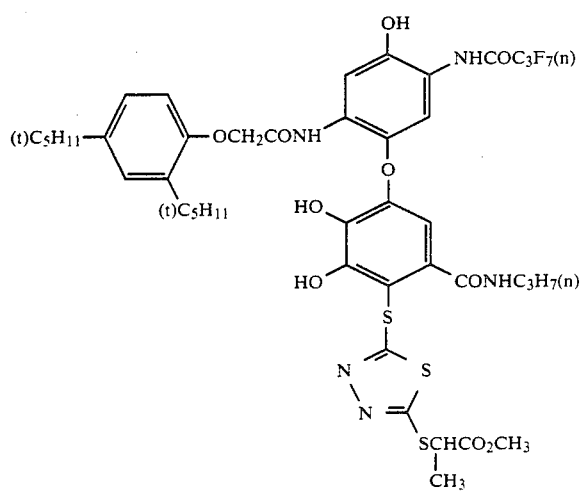
ExC-2
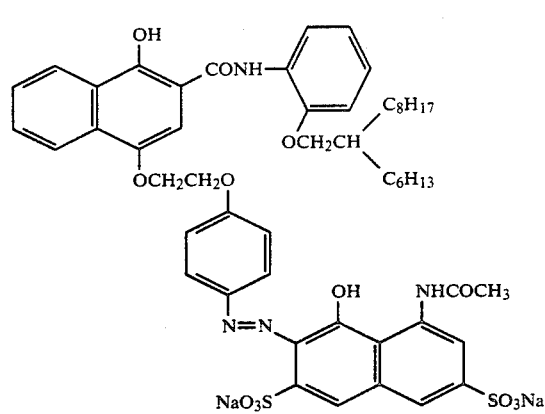
ExC-3
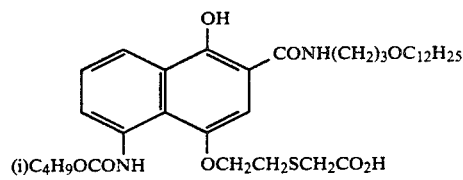
ExC-4

-continued
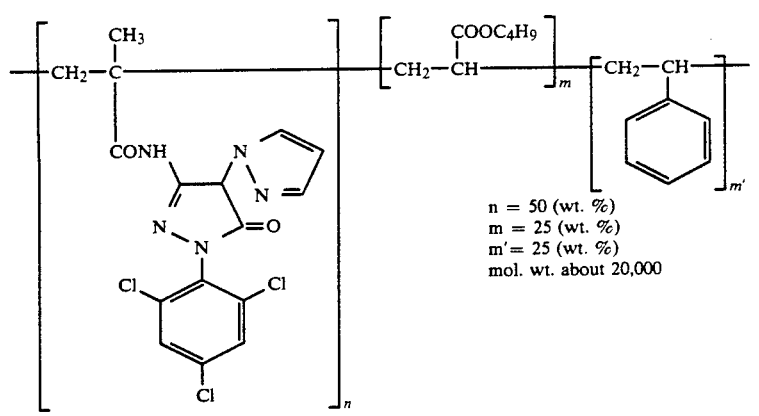
ExM-5
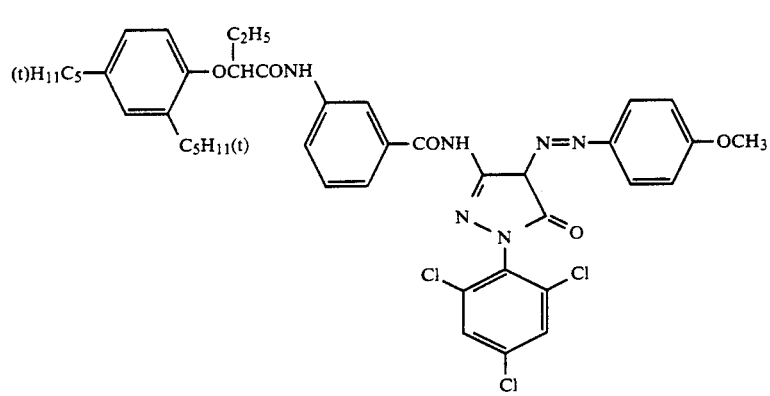
ExM-6
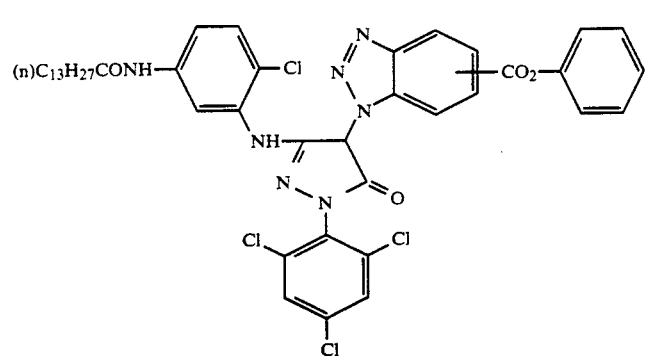
ExM-10
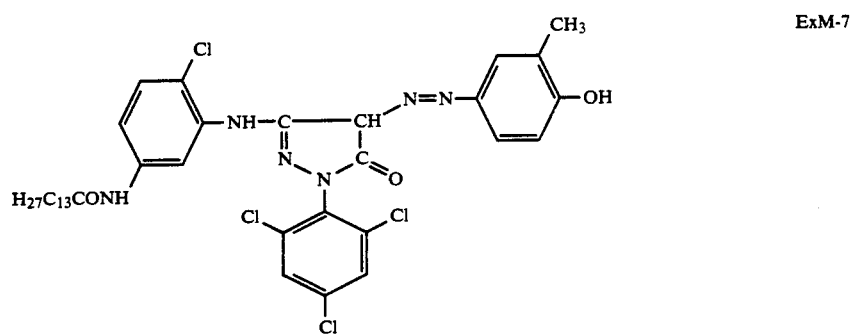
ExM-7

-continued
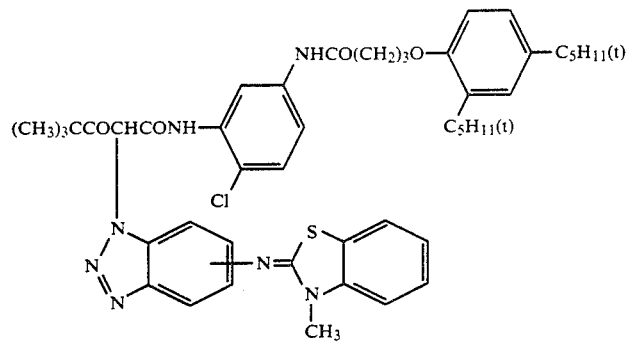
ExY-8
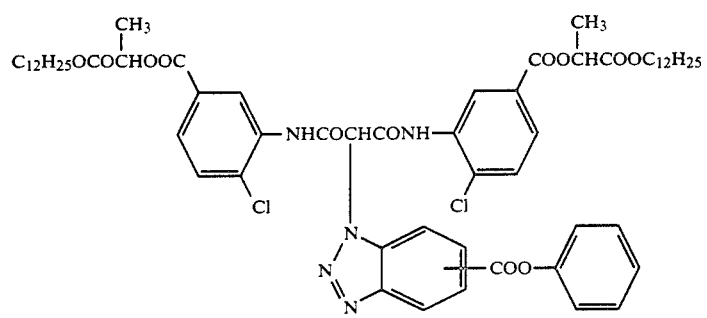
ExY-9
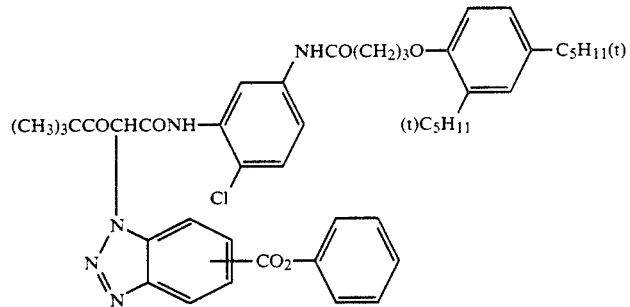
ExY-12
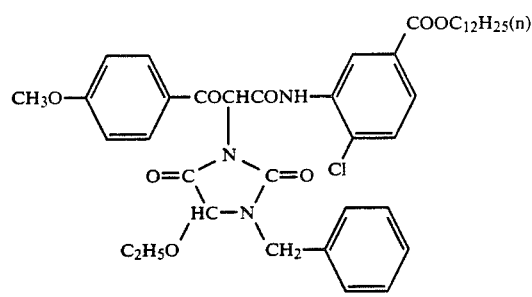
ExY-11
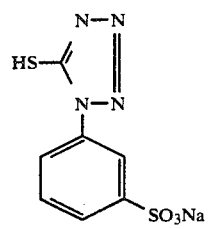
Cpd-7

-continued

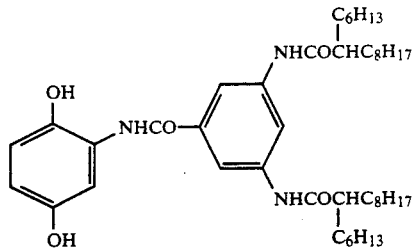 Cpd-1

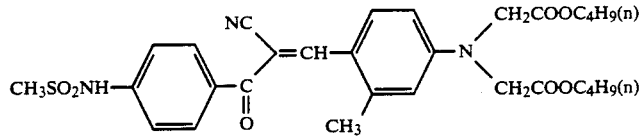 Cpd-2

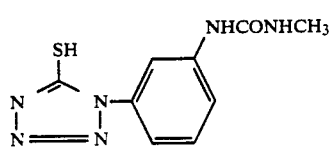 Cpd-6

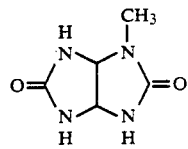 Cpd-5

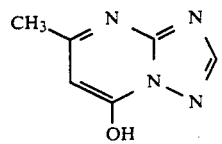 Cpd-3

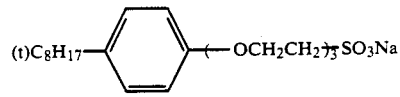 Cpd-4

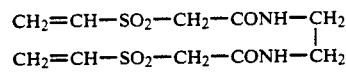 H-1

Light-Sensitive Material 501 thus-prepared was cut into a 35 m/m width strip, photographed with usual subjects and then subjected to development processing using an automatic developing machine according to the following processing steps shown in Table 7:

In the fixing tank of the automatic developing machine used, a jet stirrer as described in JP-A-62-183460, page 3 was equipped, and the light-sensitive material was processed in such a manner that the jet of the fixing

TABLE 7

| Processing Step | Processing Temperature (°C.) | Processing Time | Amount of* Replenishment (ml) | Capacity of Tank (l) |
|---|---|---|---|---|
| Color Development | 37.8 | 3 min. 15 sec. | 21 | 5 |
| Bleaching | 38.0 | 45 sec. | 4.5 | 2 |
| Fixing (1) | 38.0 | 45 sec. | Two-tank countercurrent system | 2 |
| Fixing (2) | 38.0 | 45 sec. | 30 | 2 |
| Stabilizing (1) | 38.0 | 20 sec. | Three-tank countercurrent system | 1 |
| Stabilizing (2) | 38.0 | 20 sec. | | 1 |
| Stabilizing (3) | 38.0 | 20 sec. | 35 | 1 |
| Drying | 55 | 1 min. 00 sec. | | |

*Amount of replenishment per 1 meter of 35 m/m width strip solution struck on the surface of the light-sensitive material.

The composition of each processing solution used is illustrated below.

| | Tank Solution | Replenisher |
|---|---|---|
| Color Developing Solution: | | |
| Diethylenetriaminepentaacetic Acid | 5.0 g | 6.0 g |
| Sodium Sulfite | 4.0 g | 5.0 g |
| Potassium Carbonate | 30.0 g | 37.0 g |
| Potassium Bromide | 1.3 g | 0.5 g |
| Potassium Iodide | 1.2 mg | — |
| Hydroxylamine Sulfate | 2.0 g | 3.6 g |
| 4-(N-Ethyl-N-$\beta$-hydroxyethyl-amino)-2-methylaniline Sulfate | 4.7 g | 6.2 g |
| Water to make | 1.0 l | 1.0 l |
| pH | 10.00 | 10.15 |
| Bleaching Solution: | | |
| Ferric Complex of 1,3-Diamino-propanetetraacetic Acid | 130 g (0.36 mol/l) | 190 g (0.53 mol/l) |
| 1,3-Diaminopropanetetraacetic Acid | 3.0 g | 4.0 g |
| Ammonium Bromide | 85 g | 120 g |
| Acetic Acid | 50 ml | 70 ml |
| Ammonium Nitrate | 30 g | 40 g |
| Water to make | 1.0 l | 1.0 l |
| pH | 4.3 | 3.5 |

The pH was adjusted with acetic acid and aqueous ammonia.

| Fixing Solution: | Tank Solution | Replenisher |
|---|---|---|
| 1-Hydroxyethylidene-1,1-diphosphoric Acid | 5.0 g | 7.0 g |
| Disodium Ethylenediaminetetraacetate | 0.5 g | 0.7 g |
| Sodium Sulfite | 10.0 g | 12.0 g |
| Sodium Bisulfite | 8.0 g | 10.0 g |
| Aqueous Solution of Ammonium Thiosulfate (700 g/l) | 170.0 ml | 200.0 ml |
| Ammonium Thiocyanate | 100.0 g | 150.0 g |
| Thiourea | 3.0 g | 5.0 g |
| 3,6-Dithia-1,8-octanediol | 3.0 g | 5.0 g |
| Water to make | 1.0 l | 1.0 l |
| pH | 6.5 | 6.7 |

The pH was adjusted with acetic acid and aqueous ammonia.

| Stabilizing Solution: (both mother solution and replenisher) | |
|---|---|
| Formalin (37%) | 1.2 ml |
| 5-Chloro-2-methyl-4-isothiazolin-3-one | 6.0 mg |
| 2-Methyl-4-isothiazolin-3-one | 3.0 mg |
| Surface Active Agent $C_{10}H_{21}$—O—$(CH_2CH_2O)_{10}$—H | 0.4 g |
| Ethylene Glycol | 1.0 g |
| Water to make | 1.0 l |
| pH | 5.0 to 7.0 |

The color negative film thus-obtained was printed to color paper using a color printer, and the color paper was subjected to standard development processing to prepare a color print. The color print was particularly excellent in image sharpness.

EXAMPLE 6

On a cellulose triacetate film support were coated the first layer to the fourteenth layer shown below in order to prepare a multilayer color photographic light-sensitive material which was designated Light-Sensitive Material 601.

Compositions of Light-Sensitive Layers

The components used in each layer and the coating amounts thereof in terms of g/m² are described below. The coating amount of silver halide is indicated in terms of silver coating amount.

| First Layer: Antihalation Layer | |
|---|---|
| Black colloidal silver | 0.30 |
| Gelatin | 2.50 |
| UV-1 | 0.05 |
| UV-2 | 0.10 |
| UV-3 | 0.10 |
| Solv-1 | 0.10 |
| Second Layer: Intermediate Layer | |
| Gelatin | 0.50 |
| Third Layer: Low-Speed Red-Sensitive Layer | |
| Monodisperse silver iodobromide emulsion (silver iodide: 4 mol %, cubic, average particle size: 0.3 $\mu$m, S/r: 0.15) | 0.50 |
| ExS-1 | $1.40 \times 10^{-3}$ |
| ExS-2 | $6.00 \times 10^{-5}$ |
| Gelatin | 0.80 |
| ExC-1 | 0.30 |
| Solv-2 | 0.10 |
| Fourth Layer: Medium-Speed Red-Sensitive Layer | |
| Monodisperse silver iodobromide emulsion (silver iodide: 2.5 mol %, tetradecahedral, average particle size: 0.45 $\mu$m, S/r: 0.15) | 0.50 |
| ExS-1 | $1.60 \times 10^{-3}$ |
| ExS-2 | $6.00 \times 10^{-5}$ |
| Gelatin | 1.00 |
| ExC-1 | 0.45 |
| Solv-2 | 0.20 |
| Fifth Layer: High-Speed Red-Sensitive Layer | |
| Monodisperse silver iodobromide emulsion (silver iodide: 2.5 mol %, tetradecahedral, average particle size: 0.60 $\mu$m, S/r: 0.15) | 0.30 |
| ExS-1 | $1.60 \times 10^{-3}$ |
| ExS-2 | $6.00 \times 10^{-5}$ |
| Gelatin | 0.70 |
| ExC-1 | 0.30 |
| Solv-2 | 0.12 |
| Sixth Layer: Intermediate Layer | |
| Gelatin | 1.00 |
| Cpd-1 | 0.1 |
| Solv-1 | 0.03 |
| Solv-2 | 0.08 |
| Solv-3 | 0.12 |
| Cpd-2 | 0.25 |
| Seventh Layer: Low-Speed Green-Sensitive Layer | |
| Silver iodobromide emulsion (silver iodide: 3.0 mol %, mixture of regular crystals and twin crystals, average particle size: 0.3 $\mu$m) | 0.65 |
| ExS-3 | $3.30 \times 10^{-3}$ |
| ExS-4 | $1.50 \times 10^{-3}$ |
| Gelatin | 1.50 |
| ExM-1 | 0.10 |
| ExM-2 | 0.25 |
| Solv-2 | 0.30 |
| Eighth Layer: High-Speed Green-Sensitive Layer | |
| Tabular silver iodobromide emulsion (silver iodide: 2.5 mol %, particles having a diameter/thickness ratio of 5 or more occupying 50% of the projected area of the total particles, average thickness: 0.15 $\mu$m) | 0.70 |
| ExS-3 | $1.30 \times 10^{-3}$ |
| ExS-4 | $5.00 \times 10^{-4}$ |
| Gelatin | 1.00 |
| ExM-3 | 0.25 |
| Cpd-3 | 0.10 |
| Cpd-4 | 0.05 |

| | |
|---|---|
| Solv-2 | 0.05 |
| Ninth Layer: Intermediate Layer | |
| Gelatin | 0.50 |
| Tenth Layer: Yellow Filter Layer | |
| Yellow colloidal silver | 0.10 |
| Gelatin | 1.00 |
| Cpd-1 | 0.05 |
| Solv-1 | 0.03 |
| Solv-2 | 0.07 |
| Cpd-2 | 0.10 |
| Eleventh Layer: Low-Speed Blue-Sensitive Layer | |
| Silver iodobromide emulsion (silver iodide: 2.5 mol %, mixture of regular crystals and twin crystals, average particle size: 0.7 μm) | 0.55 |
| ExS-5 | $1.00 \times 10^{-3}$ |
| Gelatin | 0.90 |
| ExY-1 | 0.50 |
| Solv-2 | 0.10 |
| Twelfth Layer: High-Speed Blue-Sensitive Layer | |
| Tabular silver iodobromide emulsion (silver iodide: 2.5 mol %, particles having a diameter/thickness ratio of 5 or more occupying 50% of the projected area of the total particles, average thickness: 0.13 μm) | 1.00 |
| ExS-5 | $1.70 \times 10^{-3}$ |
| Gelatin | 2.00 |
| ExY-1 | 1.00 |
| Solv-2 | 0.20 |
| Thirteenth Layer: Ultraviolet Light Absorbing Layer | |
| Gelatin | 1.50 |
| UV-1 | 0.02 |
| UV-2 | 0.04 |
| UV-3 | 0.04 |
| Cpd-5 | 0.30 |
| Solv-1 | 0.30 |
| Cpd-6 | 0.10 |
| Fourteenth Layer: Protective Layer | |
| Fine grain silver iodobromide (silver iodide: 1 mol %, average particle size: 0.05 μm) | 0.10 |
| Gelatin | 2.00 |
| H-1 | 0.30 |

The compounds used in the above-described layers are illustrated below.

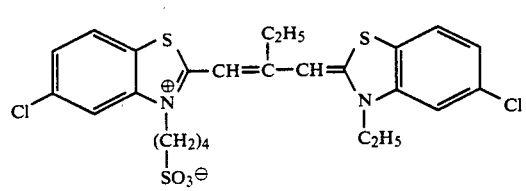

ExS-1

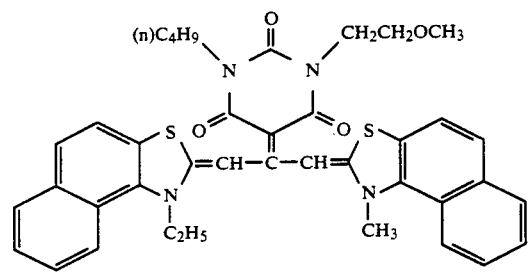

ExS-2

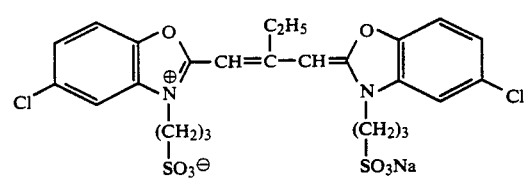

ExS-3

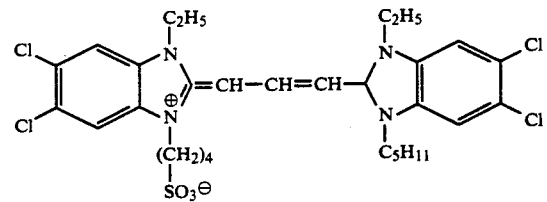

ExS-4

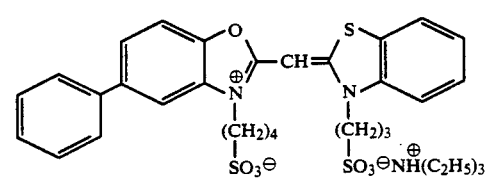

ExS-5

-continued
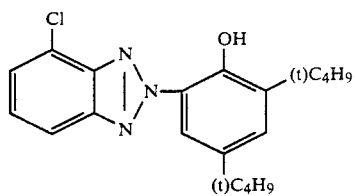 UV-1
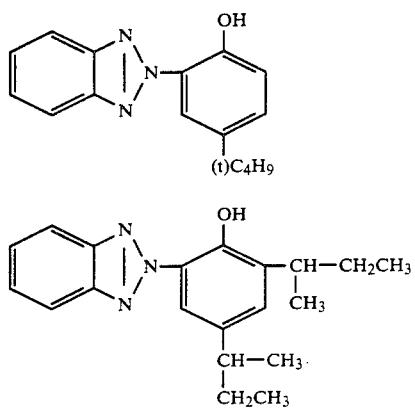 UV-2
UV-3
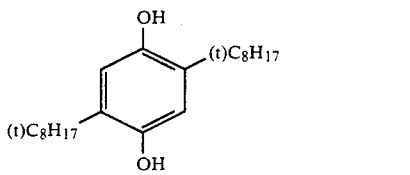 Cpd-1
Polyethyl acrylate   Cpd-2
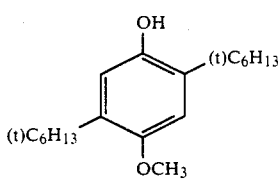 Cpd-3
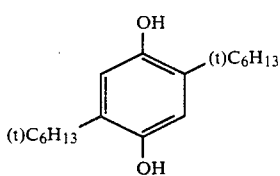 Cpd-4
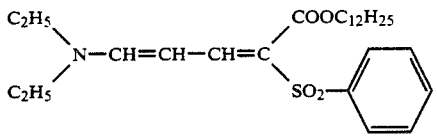 Cpd-5
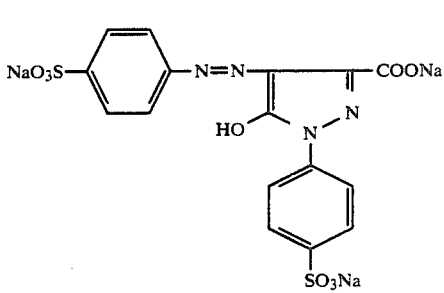 Cpd-6
(corresponding to Compound (1))   ExC-1

-continued
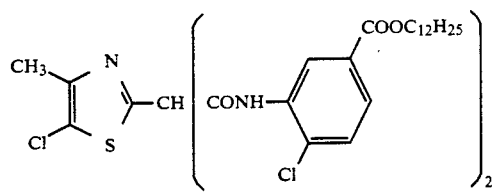
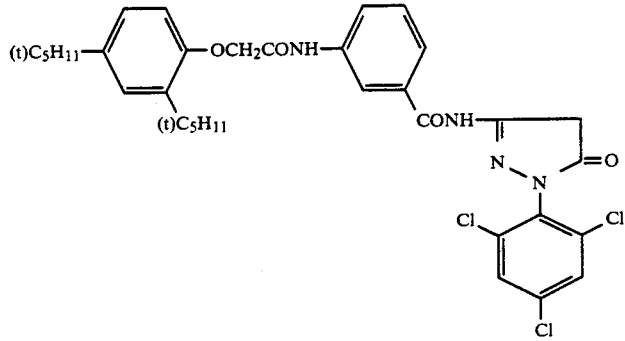
ExM-1
ExM-2
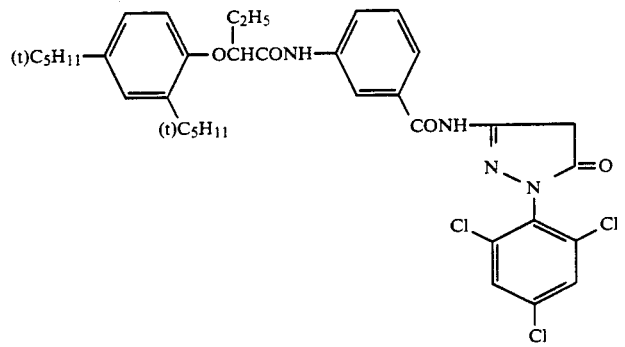
ExM-3
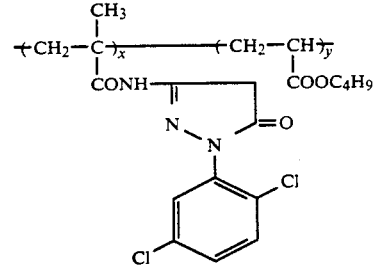
x:y = 50:50 (wt %)  mol. wt. average 20,000
ExY-1
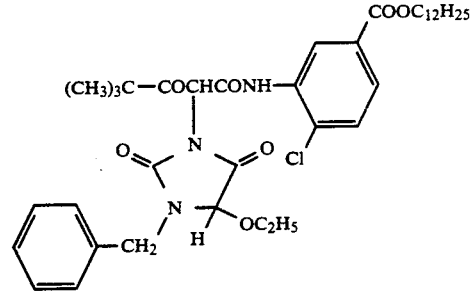
| | |
|---|---|
| Dibutyl phthalate | Solv-1 |
| Tricresyl phosphate | Solv-2 |
| Trinonyl phosphate | Solv-3 |
| 1,2-Bis(vinylsulfonylacetamido)ethane | H-1 |
Light-Sensitive Material 601 thus-prepared was cut into a 35 m/m width strip, photographed usual subjects

| Processing Step | Time | Temperature (°C.) |
|---|---|---|
| Fist Development | 6 minutes | 38 |
| Washing with Water | 2 minutes | 38 |
| Reversal | 2 minutes | 38 |
| Color Development | 6 minutes | 38 |
| Controlling | 2 minutes | 38 |
| Bleaching | 6 minutes | 38 |
| Fixing | 4 minutes | 38 |
| Washing with Water | 4 minutes | 38 |
| Stabilizing | 1 minute | 25 |

The composition of each processing solution used was as follows:

| First Developing Solution: | |
|---|---|
| Pentasodium nitrilo-N,N,N-trimethylene-phosphate | 2.0 g |
| Sodium sulfite | 30 g |
| Potassium hydroquinonemonosulfonate | 20 g |
| Potassium carbonate | 33 g |
| 1-Phenyl-4-methyl-4-hydroxymethyl-3-pyrazolidone | 2.0 g |
| Potassium bromide | 2.5 g |
| Potassium thiocyanate | 1.2 g |
| Potassium iodide | 2.0 mg |
| Water to make | 1000 ml |
| pH | 9.60 |

The pH was adjusted with hydrochloric acid or potassium hydroxide.

| Reversal Solution: | |
|---|---|
| Pentasodium nitrilo-N,N,N-trimethylene-phosphate | 3.0 g |
| Stannous chloride dihydrate | 1.0 g |
| p-Aminophenol | 0.1 g |
| Sodium hydroxide | 8 g |
| Glacial acetic acid | 15 ml |
| Water to make | 1000 ml |
| pH | 6.00 |

The pH was adjusted with hydrochloric acid or sodium hydroxide.

| Color Developing Solution: | |
|---|---|
| Pentasodium nitrilo-N,N,N-trimethylene-phosphonate | 2.0 g |
| Sodium sulfite | 7.0 g |
| Sodium tertiary phosphate 12 hydrate | 36 g |
| Potassium bromide | 1.0 g |
| Potassium iodide | 90 mg |
| Sodium hydroxide | 3.0 g |
| Citrazinic acid | 1.5 g |
| N-Ethyl-N-(β-methanesulfonamidoethyl)-3-methyl-4-aminoaniline sulfate | 11 g |
| 3,6-Dithiaoctane-1,8-diol | 1.0 g |
| Water to make | 1000 ml |
| pH | 11.80 |

The pH was adjusted with hydrochloric acid or potassium hydroxide.

| Controlling Solution: | |
|---|---|
| Disodium ethylenediaminetetraacetate dihydrate | 8.0 g |
| Sodium sulfite | 12 g |
| 1-Thioglycerol | 0.4 ml |
| Water to make | 1000 ml |

-continued

| Controlling Solution: | |
|---|---|
| pH | 6.20 |

The pH was adjusted with hydrochloric acid or sodium hydroxide.

| Bleaching Solution: | |
|---|---|
| Disodium ethylenediaminetetraacetate dihydrate | 2.0 g |
| Ammonium ethylenediaminetetraacetato ferrate dihydrate | 120 g |
| Potassium bromide | 100 g |
| Ammonium nitrate | 10 g |
| Water to make | 1000 ml |
| pH | 5.70 |

The pH was adjusted with hydrochloric acid or sodium hydroxide.

| Fixing Solution: | |
|---|---|
| Ammonium thiosulfate | 80 g |
| Sodium sulfite | 5.0 g |
| Sodium bisulfite | 5.0 g |
| Water to make | 1000 ml |
| pH | 6.60 |

The pH was adjusted with hydrochloric acid or aqueous ammonia.

| Stabilizing Solution: | |
|---|---|
| Formalin (37%) | 5.0 ml |
| Polyoxyethylene-p-mononoylphenyl ether (average degree of polymerization: 10) | 0.5 ml |
| Water to make | 1000 ml |
| pH | not adjusted |
| Washing Water | |
| City water | |

The color slide thus-obtained was excellent in sharpness and image preservability.

While the invention has been described in detail and with reference to specific embodiments thereof, it will be apparent to one skilled in the art that various changes and modifications can be made therein without departing from the spirit and scope thereof.

What is claimed is:

1. A silver halide color photographic material comprising a support having thereon at least one silver halide emulsion layer, wherein the silver halide color photographic material contains a coupler represented by the following general formula (I):

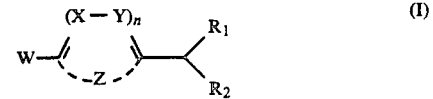

wherein X represents

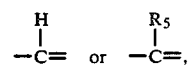

wherein $R_5$ represents a halogen atom, a straight chain, branched chain or cyclic, saturated or unsaturated aliphatic group, a heterocyclic group, a cyano group, an alkoxy group, an aryloxy group, a heterocyclic-oxy group, an acyloxy group, a carbamoyloxy group, a silyloxy group, a sulfonyloxy group, an acylamino group, an anilino group, a ureido group, an imido group, a sulfamoylamino group, an alkylthio group, an arylthio group, a heterocycli-thio group, an alkoxycarbonylamino group, an aryloxycarbonylamino group, a sulfonamido group, a carbamoyl group, an acyl group, a sulfamoyl group, a sulfonyl group, a sulfinyl group, an alkoxycarbonyl group, an aryloxycarbonyl group or an aromatic group having from 6 to 36 carbon atoms; Y represents a nitrogen atom; n represents 1 or 2, when n is 2, the two X's and two Y's may be the same or different; Z represents a non-metallic atomic group necessary to form a heterocyclic ring together with

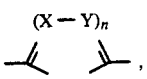

or Z represents an ether bond, or a thioether bond; W represents a hydrogen atom or a group capable of being released upon a reaction with an oxidation product of a developing agent; and $R_1$ and $R_2$ each represents a substituent, and at least one of $R_1$ and $R_2$ represents an electron attractive substituent.

2. A silver halide color photographic material as claimed in claim 1, wherein Z represents an atom or an atomic group necessary to form a 5-membered ring to an 8-membered ring together with

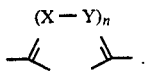

3. A silver halide color photographic material as claimed in claim 2, wherein Z represents an atom or an atomic group necessary to form a 5-membered ring together with

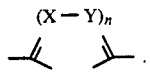

4. A silver halide color photographic material as claimed in claim 1, wherein Z represents a divalent amino group, an ether bond, a thioether bond, an alkylene group, an alkenylene group, an imino group, a sulfonyl group, a carbonyl group or a combination of two or more thereof.

5. A silver halide color photographic material as claimed in claim 1, wherein Z represents —O—, —S— or —X'=Y'— wherein X' and Y' each has the same meaning as defined for X and Y.

6. A silver halide color photographic material as claimed in claim 5, wherein Z represents —S—.

7. A silver halide color photographic material as claimed in claim 1, wherein the group capable of being released represented by W is a halogen atom, an aromatic azo group, a group wherein an aliphatic group, an aromatic group, a heterocyclic group, an aliphatic, aromatic or heterocyclic sulfonyl group or an aliphatic, aromatic or heterocyclic carbonyl group is connected to the coupling position through an oxygen, nitrogen, sulfur or carbon atom, or a heterocyclic group which is connected to the coupling position through a nitrogen atom.

8. A silver halide color photographic material as claimed in claim 1, wherein the group capable of being released represented by W is a halogen atom, an alkoxy group, an aryloxy group, an acyloxy group, an aliphatic or aromatic sulfonyloxy group, an acylamino group, an aliphatic or aromatic sulfonamido group, an alkoxycarbonyloxy group, an aryloxycarbonyloxy group, an aliphatic, aromatic or heterocyclic thio group, a carbamoylamino group, a 5-membered or 6-membered nitrogen-containing heterocyclic group, an imido group or an aromatic azo group.

9. A silver halide color photographic material as claimed in claim 1, wherein the electron attractive substituent represented by $R_1$ or $R_2$ is a substituent having the Hammet's substituent constant $o_p$ of 0 or larger.

10. A silver halide color photographic material as claimed in claim 9, wherein the substituent is a cyano group, a carbamoyl group, an alkoxycarbonyl group, an aryloxycarbonyl group, an acyl group, a sulfonyl group, a sulfamoyl group, a nitro group, fluorinated alkyl group, a sulfinyl group or an aromatic group.

11. A silver halide color photographic material as claimed in claim 1, wherein $R_1$ and $R_2$ each represents a cyano group, a carbamoyl group, an alkoxycarbonyl group, an acyl group, a sulfonyl group or a sulfamoyl group.

12. A silver halide color photographic material as claimed in claim 1, wherein at least one of $R_1$ and $R_2$ is an N-phenylcarbamoyl group.

13. A silver halide color photographic material as claimed in claim 12, wherein at least one of $R_1$ and $R_2$ is a group

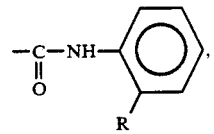

wherein R represents a group having a lone pair of electrons.

14. A silver halide color photographic material as claimed in claim 1, wherein n is 1.

15. A silver halide color photographic material as claimed in claim 1, wherein said coupler has a diffusion-resistant group.

16. A silver halide color photographic material as claimed in claim 6, wherein the coupler represented by the general formula (I) is selected from the group consisting of those represented by the following formula;

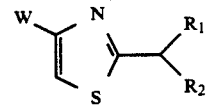

wherein W, $R_1$ and $R_2$ each has the same meaning as that in the general formula (I).

17. A silver halide color photographic material as claimed in claim 1, wherein at least one of $R_1$, $R_2$, X and Y has an organic group having at least 10 carbon atoms.

18. A silver halide color photographic material as claimed in claim 1, wherein an amount of the cyan coupler is in a range from 0.001 mol to 1 mol per mol of light-sensitive silver halide present in the silver halide emulsion layer.

19. A silver halide color photographic material as claimed in claim 1, wherein the cyan coupler is incorporated into a red-sensitive silver halide emulsion layer or a light-insensitive layer adjacent thereto.

20. A silver halide color photographic material as claimed in claim 19, wherein a red-sensitive silver halide emulsion layer contains the cyan coupler.

21. A silver halide color photographic material as claimed in claim 20, wherein the silver halide color photographic material further comprises at least one blue-sensitive silver halide emulsion layer containing at least one yellow coupler and at least one green-sensitive silver halide emulsion layer containing at least one magenta coupler.

22. A silver halide color photographic material as claimed in claim 21, wherein the blue-sensitive, green-sensitive and red-sensitive silver halide emulsion layers each comprises at least two layers having different speeds.

23. A silver halide color photographic material as claimed in claim 1, wherein the coupler is employed in a range from $2 \times 10^{-4}$ to $9 \times 10^{-4}$ mol per m$^2$.

24. A silver halide color photographic material as claimed in claim 1, wherein the coupler is employed in a range from $0.5 \times 10^{-3}$ to $9 \times 10^{-3}$ mol per m$^2$.

25. A silver halide color photographic material comprising a support having thereon at least one silver halide emulsion layer, wherein the silver halide color photographic material contains a coupler represented by the following general formula (I):

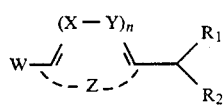

wherein X and Y each represents

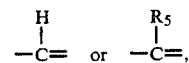

wherein $R_5$ represents a halogen atom, a straight chain, branched chain or cyclic, saturated or unsaturated aliphatic group, a heterocyclic group, a cyano group, an alkoxy group, an aryloxy group, a heterocyclic-oxy group, an acyloxy group, a carbamoyloxy group, a silyloxy group, a sulfonyloxy group, an acylamino group, an anilino group, a ureido group, an imido group, a sulfamoylamino group, an alkylthio group, a arylthio group, a heterocyclic-thio group, an alkoxycarbonylamino group, an aryloxycarbonylamino group, a sulfonamido group, a carbamoyl group, an acyl group, a sulfamoyl group, a sulfonyl group, a sulfinyl group, an alkoxycarbonyl group, an aryloxycarbonyl group or an aromatic group having from 6 to 36 carbon atoms; n represents 1 or 2, when n is 2, the two X's and two Y's may be the same or different; Z represents a non-metallic atomic group necessary to form a heterocyclic ring or aromatic ring together with

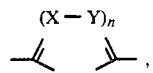

or Z represents an ether bond, or a thioether bond; W represents a hydrogen atom or a group capable of being released upon a reaction with an oxidation product of a developing agent; and $R_1$ and $R_2$ each represents a substituent, and at least one of $R_1$ and $R_2$ represents an electron attractive substituent.

* * * * *